United States Patent
Zhu et al.

(10) Patent No.: US 8,383,623 B2
(45) Date of Patent: Feb. 26, 2013

(54) PHTHALAZIN-(2H)-ONE INHIBITORS OF KINASES

(75) Inventors: Gui-Dong Zhu, Gurnee, IL (US); Virajkumar B. Gandhi, Gurnee, IL (US); Alexander R. Shoemaker, Green Oaks, IL (US); Thomas D. Penning, Elmhurst, IL (US); Jianchun Gong, Deerfield, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 13/086,580

(22) Filed: Apr. 14, 2011

(65) Prior Publication Data
US 2011/0257187 A1  Oct. 20, 2011

Related U.S. Application Data

(60) Provisional application No. 61/324,899, filed on Apr. 16, 2010.

(51) Int. Cl.
*A01N 43/58* (2006.01)
*A61K 31/50* (2006.01)
*C07D 237/30* (2006.01)

(52) U.S. Cl. .................. 514/248; 544/236; 544/237
(58) Field of Classification Search .................. 544/236, 544/237; 514/248
See application file for complete search history.

(56) References Cited

U.S. PATENT DOCUMENTS
2009/0203690 A1  8/2009  Akritopoulou-Zanze et al.

OTHER PUBLICATIONS

Pinedo et al, McMahon et al.*
Cho W.H., et al., "CDC7 Kinase Phosphorylates Serine Residues Adjacent to Acidic Amino Acids in the Minichromosome Maintenance 2 Protein," Proceedings of the National Academy of Sciences USA, 2006, vol. 103 (31), pp. 11521-11526.
Cross, L.C. et al., "IUPAC Commission on Nomenclature of Organic Chemistry: Rules for the Nomenclature of Organic Chemistry, Section E: Stereochemistry," Pure and Applied Chemistry, 1976, vol. 45, pp. 11-30.
Feng D., et al., "Inhibiting the Expression of DNA Replication-Initiation Proteins Induces Apoptosis in Human Cancer Cells," Cancer Research, 2003, vol. 63, pp. 7356-7364.
Kim J.M., et al., "Functions of Mammalian Cdc7 Kinase in Initiation/Monitoring of DNA Replication and Development," Mutation Research, 2003, vol. 532, pp. 29-40.
Kim J.M., et al., "Genetic Dissection of Mammalian Cdc7 Kinase: Cell Cycle 20 and Developmental Roles," Cell Cycle, 2004, vol. 3 (3), pp. 300-304.
Lau E., et al., "Is There a Pre-RC Checkpoint that Cancer Cells Lack?," Cell Cycle, 2006, vol. 5 (15), pp. 1602-1606.
Lau E., et al., "The Functional Role of Cdc6 in S-G2/M in Mammalian Cells," EMBO Reports, 2006, vol. 7 (4), pp. 425-430.
Lau E., et al., "The Role of Pre-Replicative Complex (pre-RC) Components in Oncogenesis," Faseb Journal, 2007, vol. 21, pp. 3786-3794.
Montagnoli A., et al., "Cdc7 Inhibition Reveals a p53- Dependent Replication Checkpoint that is Defective in Cancer Cells," Cancer Research, 2004, vol. 64, pp. 7110-7116.
Montagnoli A., et al., "Identification of Mcm2 Phosphorylation Sites by S-Phase-Regulating Kinases," The Journal of Biological Chemistry, 2006, vol. 281 (15), pp. 10281-10290.
Stillman B., "Origin Recognition and the Chromosome Cycle," FEBS Letters, 2005, vol. 579, pp. 877-884.
Sutton, V.R. et al., "Bcl-2 Prevents Apoptosis Induced by Perforin and Granzyme B, but Not That Mediated by Whole Cytotoxic Lymphocytes," Journal of Immunology, 1997, vol. 158, pp. 5783-5790.
Tsuji T., et al., "Essential Role of Phosphorylation of MCM2 by Cdc7/Dbf4 in the Initiation of DNA Replication in Mammalian Cells," Molecular Biology of the Cell, 2006, vol. 17, pp. 4459-4472.
International Search Report and Written Opinion for Application No. PCT/US2011/032433, mailed on May 31, 2011, 9 pages.

* cited by examiner

*Primary Examiner* — Paul V. Ward
(74) *Attorney, Agent, or Firm* — Susan L. Steele

(57) ABSTRACT

The present invention relates to compounds of formula (I) or pharmaceutical acceptable salts,

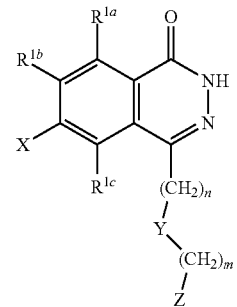

Formula (I)

wherein $R^{1a}$, $R^{1b}$, $R^{1c}$, X, Y, Z, n, and m are defined in the description. The present invention relates also to compositions containing said compounds which are useful for inhibiting kinases such as Cdc7 and methods of treating diseases such as cancer.

8 Claims, No Drawings

PHTHALAZIN-(2H)-ONE INHIBITORS OF KINASES

CROSS-REFERENCE TO RELATED APPLICATIONS

This application claims priority to U.S. Provisional Application Ser. No. 61/324,899 filed Apr. 16, 2010, which is incorporated by reference in its entirety.

BACKGROUND OF THE INVENTION

Eukaryotic cells divide by a directed, step-wise process referred to as the cell cycle. Cells must first replicate their DNA in S phase before separating their sister chromatids in mitosis (karyokinesis) and splitting off into two daughter cells (cytokinesis). In mammalian cells, DNA replication must be initiated at multiple sites (replication origins) throughout the genome to ensure that all the genetic material is duplicated prior to mitosis. To maintain genome integrity, DNA must be replicated only once per cell cycle, and so this process is highly regulated and governed by checkpoints. Before replication is initiated, origins must be licensed through the formation of pre-replication complexes (pre-RCs) in early G1.

Formation of pre-RCs involves the step-wise binding of the origin recognition complex (ORC) to origins followed by the binding of the loading factors Cdc6 and Cdt1. These proteins then recruit the putative DNA replicative helicase complex, MCM2-7. Once this pre-RC is formed, replication initiation requires the activation of S-phase-promoting serine/threonine kinases, Cyclin/Cdks and Cdc7/Dbf4. These kinases consist of an enzymatic subunit (CDKs and Cdc7) and a regulatory sub-unit (Cyclins for CDKs; Dbf4 or Drf1 for Cdc7). They phosphorylate multiple MCMs in pre-RCs in a sequential manner, thereby activating the helicase and recruiting other DNA replication factors (Cdc45, GINS complex, etc.) for DNA synthesis (for reviews, see Kim et al., 2003; Kim et al., 2004; Lau et al., 2006; Lau et al., 2007; Stillman, 2005). MCM2 Serine-40 and Serine-53 are well-characterized phosphorylation sites for Cdc7/Dbf4 (Cho et al., 2006; Montagnoli et al., 2006; Tsuji et al., 2006).

Inhibiting regulators of replication initiation, such as Cdc6, Cdc7/Dbf4 or Cdc7/Drf1, has lethal consequences in cancerous cells, whereas normal cells are able to arrest and resume normal divisions once initiation activity is restored (Feng et al., 2003; Montagnoli et al., 2004; see Lau and Jiang, 2006, for review). Small molecule inhibitors of the protein kinase Cdc7 are thus attractive candidates for therapeutic intervention in cancer, inflammation and other cell proliferative disorders.

SUMMARY OF THE INVENTION

The present invention has numerous embodiments. One embodiment of this invention, therefore, pertains to compounds that have formula (I)

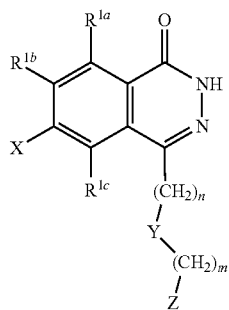

Formula (I)

wherein $R^{1a}$, $R^{1b}$, $R^{1c}$, X, Y, Z, n, and m are as defined below and subsets therein.

Also provided are pharmaceutically acceptable compositions, comprising a therapeutically effective amount of a compound of formula (I) and a pharmaceutically acceptable salt in combination with a pharmaceutically suitable carrier.

One embodiment is directed to a method of treating cancer in a mammal comprising administering thereto a therapeutically acceptable amount of a compound or pharmaceutically acceptable salt of formula (I). Another embodiment pertains to a method of decreasing tumor volume in a mammal comprising administering thereto a therapeutically acceptable amount of a compound or pharmaceutically acceptable salt of formula (I).

DETAILED DESCRIPTION OF THE INVENTION

This detailed description is intended only to acquaint others skilled in the art with Applicants' invention, its principles, and its practical application so that others skilled in the art may adapt and apply the invention in its numerous forms, as they may be best suited to the requirements of a particular use. This description and its specific examples are intended for purposes of illustration only. This invention, therefore, is not limited to the embodiments described in this patent application, and may be variously modified.

Abbreviations and Definitions

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. In this application, the use of "or" means "and/or" unless stated otherwise. Furthermore, the use of the term "including", as well as other forms, such as "includes" and "included", is not limiting. With reference to the use of the words "comprise" or "comprises" or "comprising" in this patent application (including the claims), Applicants note that unless the context requires otherwise, those words are used on the basis and clear understanding that they are to be interpreted inclusively, rather than exclusively, and that Applicants intend each of those words to be so interpreted in construing this patent application, including the claims below. For a variable that occurs more than one time in any substituent or in the compound of the invention or any other formulae herein, its definition on each occurrence is independent of its definition at every other occurrence. Combinations of substituents are permissible only if such combinations result in stable compounds. Stable compounds are compounds which can be isolated in a useful degree of purity from a reaction mixture.

It is meant to be understood that proper valences are maintained for all combinations herein, that monovalent moieties having more than one atom are attached through their left ends, and that divalent moieties are drawn from left to right.

As used in the specification and the appended claims, unless specified to the contrary, the following terms have the meaning indicated:

The term "alkyl" (alone or in combination with another term(s)) means a straight-or branched-chain saturated hydrocarbyl substituent typically containing from 1 to about 10 carbon atoms; or in another embodiment, from 1 to about 8 carbon atoms; in another embodiment, from 1 to about 6 carbon atoms; and in another embodiment, from 1 to about 4 carbon atoms. Examples of such substituents include methyl, ethyl, n-propyl, isopropyl, n-butyl, isobutyl, sec-butyl, tert-butyl, pentyl, iso-amyl, and hexyl and the like.

The term "alkenyl" (alone or in combination with another term(s)) means a straight- or branched-chain hydrocarbyl substituent containing one or more double bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethenyl (vinyl), 2-propenyl, 3-propenyl, 1,4-pentadienyl, 1,4-butadienyl, 1-butenyl, 2-butenyl, and 3-butenyl and the like.

The term "alkynyl" (alone or in combination with another term(s)) means a straight- or branched-chain hydrocarbyl substituent containing one or more triple bonds and typically from 2 to about 10 carbon atoms; or in another embodiment, from 2 to about 8 carbon atoms; in another embodiment, from 2 to about 6 carbon atoms; and in another embodiment, from 2 to about 4 carbon atoms. Examples of such substituents include ethynyl, 2-propynyl, 3-propynyl, 2-butynyl, and 3-butynyl and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single-ring (monocyclic) or polycyclic ring structure.

A carbocyclyl may be a single ring structure, which typically contains from 3 to 8 ring atoms, more typically from 3 to 6 ring atoms, and even more typically 5 to 6 ring atoms. Examples of such single-ring carbocyclyls include cyclopropyl (cyclopropanyl), cyclobutyl (cyclobutanyl), cyclopentyl (cyclopentanyl), cyclopentenyl, cyclopentadienyl, cyclohexyl (cyclohexanyl), cyclohexenyl, cyclohexadienyl, and phenyl. A carbocyclyl may alternatively be polycyclic (i.e., may contain more than one ring). Examples of polycyclic carbocyclyls include bridged, fused, and spirocyclic carbocyclyls. In a spirocyclic carbocyclyl, one atom is common to two different rings. An example of a spirocyclic carbocyclyl is spiropentanyl. In a bridged carbocyclyl, the rings share at least two common non-adjacent atoms. Examples of bridged carbocyclyls include bicyclo[2.2.1]heptanyl, bicyclo[2.2.1]hept-2-enyl, and adamantanyl. In a fused-ring carbocyclyl system, two or more rings may be fused together, such that two rings share one common bond. Examples of two- or three-fused ring carbocyclyls include naphthalenyl, tetrahydronaphthalenyl(tetralinyl), indenyl, indanyl(dihydroindenyl), anthracenyl, phenanthrenyl, and decalinyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 8 carbon ring atoms and more typically from 3 to 6 ring atoms. Examples of single-ring cycloalkyls include cyclopropyl, cyclobutyl, cyclopentyl, and cyclohexyl. A cycloalkyl may alternatively be polycyclic or contain more than one ring. Examples of polycyclic cycloalkyls include bridged, fused, and spirocyclic carbocyclyls.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$-$C_y$-", wherein x is the minimum and y is the maximum number of carbon atoms in the substituent. Thus, for example, "$C_1$-$C_6$-alkyl" refers to an alkyl substituent containing from 1 to 6 carbon atoms. Illustrating further, $C_3$-$C_8$-cycloalkyl means a saturated hydrocarbyl ring containing from 3 to 8 carbon ring atoms.

The term "hydrogen" (alone or in combination with another term(s)) means a hydrogen radical, and may be depicted as —H.

The term "hydroxy" (alone or in combination with another term(s)) means —OH.

The term "carboxy" (alone or in combination with another term(s)) means —C(O)—OH.

The term "amino" (alone or in combination with another term(s)) means —$NH_2$.

The term "halogen" or "halo" (alone or in combination with another term(s)) means a fluorine radical (which may be depicted as —F), chlorine radical (which may be depicted as —Cl), bromine radical (which may be depicted as —Br), or iodine radical (which may be depicted as —I).

If a substituent is described as being "substituted", a non-hydrogen radical is in the place of hydrogen radical on a carbon or nitrogen of the substituent. Thus, for example, a substituted alkyl substituent is an alkyl substituent in which at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitution on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

This patent application uses the terms "substituent" and "radical" interchangeably.

The prefix "halo" indicates that the substituent to which the prefix is attached is substituted with one or more independently selected halogen radicals. For example, haloalkyl means an alkyl substituent in which at least one hydrogen radical is replaced with a halogen radical. Examples of haloalkyls include chloromethyl, 1-bromoethyl, fluoromethyl, difluoromethyl, trifluoromethyl, and 1,1,1-trifluoroethyl. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical.

The term "carbonyl" (alone or in combination with another term(s)) means —C(O)—.

The term "aminocarbonyl" (alone or in combination with another term(s)) means —C(O)—NH$_2$.

The term "oxo" (alone or in combination with another term(s)) means (=O).

The term "oxy" (alone or in combination with another term(s)) means an ether substituent, and may be depicted as —O—.

The term "alkylhydroxy" (alone or in combination with another term(s)) means -alkyl-OH.

The term "alkylamino" (alone or in combination with another term(s)) means -alkyl-NH$_2$.

The term "alkyloxy" (alone or in combination with another term(s)) means an alkylether substituent, i.e., —O-alkyl. Examples of such a substituent include methoxy (—O—CH$_3$), ethoxy, n-propoxy, isopropoxy, n-butoxy, iso-butoxy, sec-butoxy, and tert-butoxy.

The term "alkylcarbonyl" (alone or in combination with another term(s)) means —C(O)-alkyl.

The term "aminoalkylcarbonyl" (alone or in combination with another term(s)) means —C(O)-alkyl—NH$_2$.

The term "alkyloxycarbonyl" (alone or in combination with another term(s)) means —C(O)—O-alkyl.

The term "carbocyclylcarbonyl" (alone or in combination with another term(s)) means —C(O)-carbocyclyl.

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl.

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl.

The term "carbocyclylalkyloxycarbonyl" (alone or in combination with another term(s)) means —C(O)—O-alkyl-carbocyclyl.

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl-S-alkyl (alkyl-sulfanyl-alkyl).

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—.

The term "sulfonyl" (alone or in combination with another term(s)) means —S(O)$_2$—.

The term "aminosulfonyl" (alone or in combination with another term(s)) means —S(O)$_2$—NH$_2$.

The term "sulfinyl" or "sulfoxido" (alone or in combination with another term(s)) means —S(O)—.

The term "heterocyclyl" (alone or in combination with another term(s)) means a saturated (i.e., "heterocycloalkyl"), partially saturated (i.e., "heterocycloalkenyl"), or completely unsaturated (i.e., "heteroaryl") ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur. A heterocyclyl may be a single-ring (monocyclic) or polycyclic ring structure.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofuranyl, tetrahydrofuranyl, thiophenyl (thiofuranyl), dihydrothiophenyl, tetrahydrothiophenyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, oxazolidinyl, isoxazolidinyl, isoxazolyl, thiazolyl, isothiazolyl, thiazolinyl, isothiazolinyl, thiazolidinyl, isothiazolidinyl, thiodiazolyl, oxadiazolyl (including 1,2,3-oxadiazolyl, 1,2,4-oxadiazolyl, 1,2,5-oxadiazolyl (furazanyl), or 1,3,4-oxadiazolyl), oxatriazolyl (including 1,2,3,4-oxatriazolyl or 1,2,3,5-oxatriazolyl), dioxazolyl (including 1,2,3-dioxazolyl, 1,2,4-dioxazolyl, 1,3,2-dioxazolyl, or 1,3,4-dioxazolyl), oxathiazolyl, oxathiolyl, oxathiolanyl, pyranyl, dihydropyranyl, thiopyranyl, tetrahydrothiopyranyl, pyridinyl (azinyl), piperidinyl, diazinyl (including pyridazinyl (1,2-diazinyl), pyrimidinyl (1,3-diazinyl), or pyrazinyl (1,4-diazinyl)), piperazinyl, triazinyl (including 1,3,5-triazinyl, 1,2,4-triazinyl, and 1,2,3-triazinyl)), oxazinyl (including 1,2-oxazinyl, 1,3-oxazinyl, or 1,4-oxazinyl)), oxathiazinyl (including 1,2,3-oxathiazinyl, 1,2,4-oxathiazinyl, 1,2,5-oxathiazinyl, or 1,2,6-oxathiazinyl)), oxadiazinyl (including 1,2,3-oxadiazinyl, 1,2,4-oxadiazinyl, 1,4,2-oxadiazinyl, or 1,3,5-oxadiazinyl)), morpholinyl, azepinyl, oxepinyl, thiepinyl, and diazepinyl.

A heterocyclyl may alternatively be polycyclic (i.e., may contain more than one ring). Examples of polycyclic heterocyclyls include bridged, fused, and spirocyclic heterocyclyls. In a spirocyclic heterocyclyl, one atom is common to two different rings. In a bridged heterocyclyl, the rings share at least two common non-adjacent atoms. In a fused-ring heterocyclyl, two or more rings may be fused together, such that two rings share one common bond. Examples of fused ring heterocyclyls containing two or three rings include indolizinyl, pyranopyrrolyl, 4H-quinolizinyl, purinyl, naphthyridinyl, pyridopyridinyl (including pyrido[3,4]-N-pyridinyl, pyrido[3,2]-N-pyridinyl, or pyrido[4,3]-N-pyridinyl), and pteridinyl. Other examples of fused-ring heterocyclyls include benzo-fused heterocyclyls, such as indolyl, isoindolyl (isobenzazolyl, pseudoisoindolyl), indoleninyl (pseudoindolyl), isoindazolyl (benzpyrazolyl), benzazinyl (including quinolinyl (1-benzazinyl) or isoquinolinyl (2-benzazinyl)), phthalazinyl, quinoxalinyl, quinazolinyl, benzodiazinyl (including cinnolinyl (1,2-benzodiazinyl) or quinazolinyl (1,3-benzodiazinyl)), benzopyranyl (including chromanyl or isochromanyl), benzoxazinyl (including 1,3,2-benzoxazinyl, 1,4,2-benzoxazinyl, 2,3,1-benzoxazinyl, or 3,1,4-benzoxazinyl), and benzisoxazinyl (including 1,2-benzisoxazinyl or 1,4-benzisoxazinyl).

The term "heterocycloalkyl" (alone or in combination with another term(s)) means a saturated heterocyclyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridyl, pyrazyl, pyrimidinyl, pyridazinyl, and 1,3,5-, 1,2,4- or 1,2,3-triazinyl; 5-membered ring substituents such as imidazyl, furanyl, thiophenyl, pyrazolyl, oxazolyl, isoxazolyl, thiazolyl, 1,2,3-, 1,2,4-, 1,2,5-, or 1,3,4-oxadiazolyl and isothiazolyl; 6/5-membered fused ring substituents such as benzothiofuranyl, benzisoxazolyl, benzoxazolyl, purinyl, and anthranilyl; and 6/6-membered fused rings such as benzopyranyl, quinolinyl, isoquinolinyl, cinnolinyl, quinazolinyl, and benzoxazinyl.

A prefix attached to a multi-component substituent only applies to the first component. To illustrate, the term "alkylcycloalkyl" contains two components: alkyl and cycloalkyl. Thus, the $C_1$-$C_6$- prefix on $C_1$-$C_6$-alkylcycloalkyl means that the alkyl component of the alkylcycloalkyl contains from 1 to 6 carbon atoms; the $C_1$-$C_6$-prefix does not describe the cycloalkyl component. To illustrate further, the prefix "halo" on haloalkyloxyalkyl indicates that only the alkyloxy component of the alkyloxyalkyl substituent is substituted with one or more halogen radicals. If halogen substitution may alternatively or additionally occur on the alkyl component, the substituent would instead be described as "halogen-substituted alkyloxyalkyl" rather than "haloalkyloxyalkyl." And finally, if the halogen substitution may only occur on the alkyl component, the substituent would instead be described as "alkyloxyhaloalkyl."

The terms "treat", "treating" and "treatment" refer to a method of alleviating or abrogating a disease and/or its attendant symptoms.

The terms "prevent", "preventing" and "prevention" refer to a method of preventing the onset of a disease and/or its attendant symptoms or barring a subject from acquiring a disease. As used herein, "prevent", "preventing" and "prevention" also include delaying the onset of a disease and/or its attendant symptoms and reducing a subject's risk of acquiring a disease.

The term "therapeutically effective amount" refers to that amount of the compound being administered sufficient to prevent development of or alleviate to some extent one or more of the symptoms of the condition or disorder being treated.

The term "modulate" refers to the ability of a compound to increase or decrease the function, or activity, of a kinase. "Modulation", as used herein in its various forms, is intended to encompass antagonism, agonism, partial antagonism and/or partial agonism of the activity associated with kinase. Kinase inhibitors are compounds that, e.g., bind to, partially or totally block stimulation, decrease, prevent, delay activation, inactivate, desensitize, or down regulate signal transduction. Kinase activators are compounds that, e.g., bind to, stimulate, increase, open, activate, facilitate, enhance activation, sensitize or up regulate signal transduction.

The term "composition" as used herein is intended to encompass a product comprising the specified ingredients in the specified amounts, as well as any product which results, directly or indirectly, from combination of the specified ingredients in the specified amounts. By "pharmaceutically acceptable" it is meant the carrier, diluent or excipient must be compatible with the other ingredients of the formulation and not deleterious to the recipient thereof.

The "subject" is defined herein to include animals such as mammals, including, but not limited to, primates (e.g., humans), cows, sheep, goats, horses, dogs, cats, rabbits, rats, mice and the like. In preferred embodiments, the subject is a human.

Compounds

In one aspect, the present invention provides compounds of formula (I)

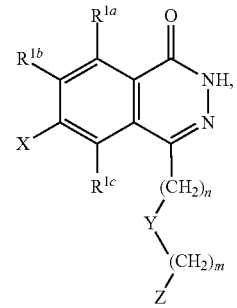

Formula (I)

wherein $R^{1a}$, $R^{1b}$, and $R^{1c}$ are independently hydrogen, hydroxy, nitro, halogen, cyano, trifluoromethyl, trifluoromethoxy, $C_{1-4}$-alkyl, —$OR^a$, or —$NR^bR^e$;

X is heteroaryl, which is optionally substituted with one or more $R^5$;

n is 0, 1, 2, or 3; provided that when n is 1, 2, or 3, m is 0;
m is 0, 1, 2, or 3; provided that when m is 1, 2, or 3, n is 0;
Y is a bond, —O—, —C(O)—, —(O)C—, —C(O)O—, —OC(O)—, —$NR^e$—, —$NR^eC(O)$—, —$C(O)NR^e$—, —$NR^eC(O)NR^f$—, —$SO_2NR^e$—, or —$NR^eSO_2$—;

Z is $C_{3-8}$-cycloalkyl, heterocycloalkyl, aryl, or heteroaryl, wherein the $C_{3-8}$-cycloalkyl, heterocycloalkyl, aryl, and heteroaryl are optionally substituted with one or more $R^6$;

$R^5$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^d$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^g$, —$C(O)R^g$, —$C(O)OR^g$, —$OC(O)R^g$, —$NR^hR^1$, —$NR^hC(O)R^g$, —$NHSO_2R^g$, —$NHC(O)NHR^h$, —$C(O)NR^hR^i$; and wherein (b) the $R^5$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^j$, —$C(O)R^j$, —$C(O)OR^j$, —$OC(O)R^j$, —$NR^kR^l$, —$NR^kC(O)R^j$, —$NHC(O)NHR^k$, —$NHSO_2R^j$, —$C(O)NR^kR^l$, —$SR^j$, —$S(O)R^j$, —$SO_2R^j$, —$SO_2NR^kNR^l$, —$CF_3$, —$CF_2CF_3$, —$OCF_3$, and —$OCF_2CF_3$;

$R^6$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^d$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^6$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^g$, —$C(O)R^g$, —$C(O)OR^g$, —$OC(O)R^g$, —$NR^hR^i$, —$NR^hC(O)R^g$, —$NHSO_2R^g$, —$NHC(O)NHR^h$, —$C(O)NR^hR^i$; and wherein (b) the $R^6$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^j$, —$C(O)R^j$, —$C(O)OR^j$, —$OC(O)R^j$, —$NR^kR^l$, —$NR^kC(O)R^j$, —$NHC(O)NHR^k$, —$NHSO_2R^j$, —C(O)NR$^k$R$^l$, —SR$^j$, —S(O)R$^j$, —SO$_2$R$^j$, —SO$_2$NR$^k$NR$^l$, —CF$_3$, —CF$_2$CF$_3$, —OCF$_3$, and —OCF$_2$CF$_3$;

R$^a$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), —O(C$_{1-8}$-alkyl)NH$_2$, and —N(C$_{1-8}$-alkyl)$_2$;

R$^b$ and R$^c$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^b$ and R$^c$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^d$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, aryl-(C$_{1-8}$-alkyl)-, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$; wherein the aryl, aryl-(C$_{1-8}$-alkyl)-, heterocyclyl, and C$_{3-8}$-cycloalkyl, alone or as part of another group, are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^e$ and R$^f$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^e$ and R$^f$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^g$ at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^h$ and R$^i$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^h$ and R$^i$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^j$, at each occurrence, is selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, wherein the C$_{1-8}$-alkyl, C$_{2-8}$-alkenyl, C$_{2-8}$-alkynyl, aryl, heterocyclyl, and C$_{3-8}$-cycloalkyl are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

R$^k$ and R$^l$, at each occurrence, are independently selected from the group consisting of hydrogen, C$_{1-8}$-alkyl, C$_{2-8}$-alkenyl, C$_{2-8}$-alkynyl, aryl, heterocyclyl, and C$_{3-8}$-cycloalkyl, and optionally, R$^k$ and R$^l$ can be joined together to form a 4-7 membered heterocycloalkyl ring, wherein the C$_{1-8}$-alkyl, C$_{2-8}$-alkenyl, C$_{2-8}$-alkynyl, aryl, heterocyclyl, C$_{3-8}$-cycloalkyl, and 4-7 membered heterocycloalkyl ring are optionally substituted with one or more substituents independently selected from the group consisting of C$_{1-8}$-alkyl, aryl, heterocyclyl, C$_{3-8}$-cycloalkyl, halogen, cyano, oxo, hydroxy, C$_{1-8}$-alkoxy, —NH$_2$, —NH(C$_{1-8}$-alkyl), and —N(C$_{1-8}$-alkyl)$_2$;

or a pharmaceutically acceptable salt thereof.

In one embodiment of formula (I), R$^{1a}$, R$^{1b}$, and R$^{1c}$ are hydrogen. In another embodiment of formula (I), R$^{1b}$ and R$^{1c}$ are hydrogen and R$^{1a}$ is hydroxy, nitro, halogen, cyano, trifluoromethyl, trifluoromethoxy, C$_{1-4}$-alkyl, —OR$^a$, or —NR$^b$R$^c$. In another embodiment of formula (I), R$^1$a and R$^{1c}$ are hydrogen and R$^{1b}$ is hydroxy, nitro, halogen, cyano, trifluoromethyl, trifluoromethoxy, C$_{1-4}$-alkyl, —OR$^a$, or —NR$^b$R$^c$. In another embodiment of formula (I), R$^{1a}$ and R$^{1b}$ are hydrogen and R$^{1c}$ is hydroxy, nitro, halogen, cyano, trifluoromethyl, trifluoromethoxy, C$_{1-4}$-alkyl, —OR$^a$, or —NR$^b$R$^c$.

In one embodiment of formula (I), X is heteroaryl, which is unsubstituted. In another embodiment of formula (I), X is heteroaryl, which is substituted with one or more R$^5$ In another embodiment of formula (I), X is a 5- or 6- membered heteroaryl selected from the group consisting of pyridyl, pyrazyl, pyrimidinyl, pyridazinyl 1,3,5-triazinyl, 1,2,4-triazinyl, 1,2,3-triazinyl, imidazyl, and pyrazolyl. In yet another embodiment of formula (I), X is fused ring heteroaryl selected from the group consisting of pyrrolopyridinyl, pyrrolopyrazinyl, indoyl, isoindoyl, azaindolyl, purinyl, quinolinyl, isoquinolinyl, cinnolinyl, and quinazolinyl.

In another embodiment of formula (I), X is

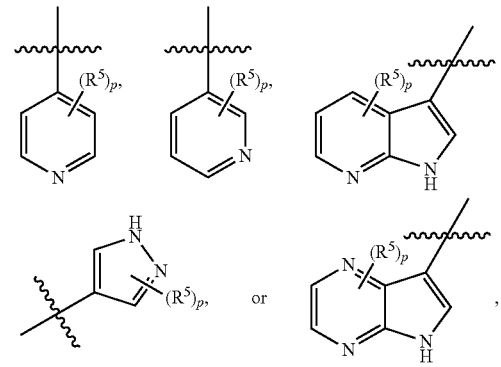

wherein p is 0, 1, or 2. In a preferred embodiment, p is 0.

In one embodiment of formula (I), n is 0, and m is 0. In another embodiment of formula (I), n is 1, and m is 0. In another embodiment of formula (I), n is 2, and m is 0. In another embodiment of formula (I), n is 3, and m is 0.

In one embodiment of formula (I), n is 0, and m is 1. In another embodiment of formula (I), n is 0, and m is 2. In another embodiment of formula (I), n is 0, and m is 3.

In one embodiment of formula (I), Y is a bond, —O—, —C(O)—, —(O)C—, —C(O)O—, —OC(O)—, —NR$^c$—, —NR$^c$C(O)—, —C(O)NR$^c$—, —NR$^c$C(O)NR$^f$—, —SO$_2$NR$^e$—, or —NR$^e$SO$_2$—. In another embodiment of formula (I), Y is a bond. In another embodiment of formula (I), n is 1, m is 0, and Y is a bond.

In another embodiment of formula (I), Z is heterocycloalkyl, which is optionally substituted with one or more R$^6$. In another embodiment of formula (I), Z is heterocycloalkyl, which is substituted with one or more R$^6$. In another embodiment of formula (I), Z is heterocycloalkyl, which is unsubstituted. In another embodiment of formula (I), Z is tetrahydrofuranyl, tetrahydrothiophenyl, pyrrolidinyl, pyrazolidinyl, piperidinyl, or piperazinyl.

In another embodiment of formula (I), Z is aryl, which is optionally substituted with one or more R$^6$. In another embodiment of formula (I), Z is aryl, which is substituted with one or more R$^6$. In another embodiment of formula (I), Z is aryl, which is unsubstituted. In another embodiment of formula (I), Z is phenyl, naphthalenyl, or indenyl.

In another embodiment of formula (I), Z is heteroaryl, which is optionally substituted with one or more R$^6$. In another embodiment of formula (I), Z is heteroaryl, which is substituted with one or more R$^6$. In another embodiment of formula (I), Z is heteroaryl, which is unsubstituted. In another embodiment of formula (I), Z is furanyl, thiophenyl, pyrrolyl, imidazolyl, pyrazolyl, triazolyl, tetrazolyl, oxazolyl, isoxazolyl, thiazolyl, isothiazolyl, thiadiazolyl, oxadiazolyl, pyridinyl, pyrimidinyl, pyrazinyl, or triazinyl.

In another embodiment of formula (I), Z is selected from the group consisting of

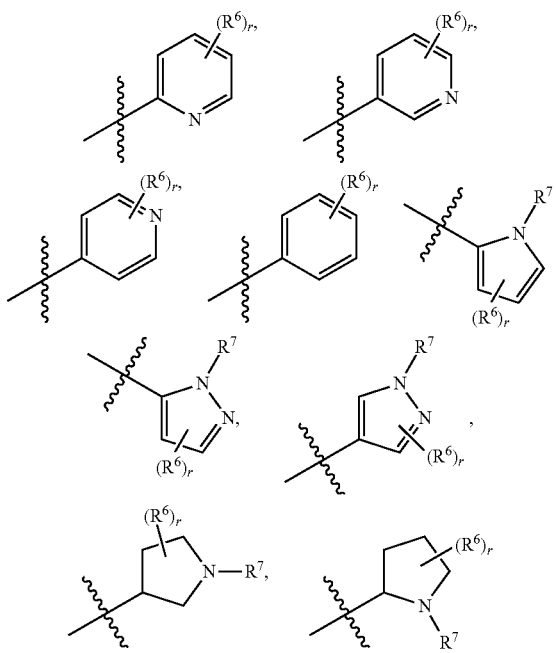

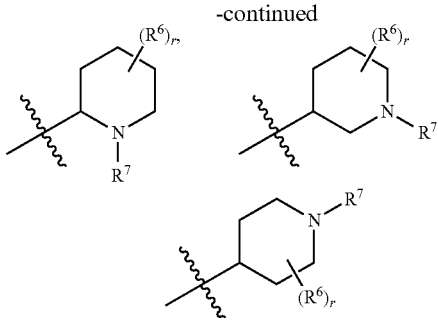

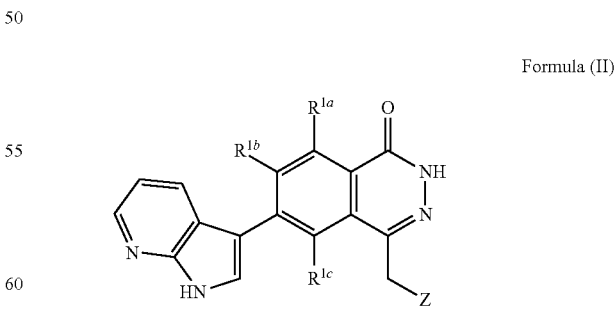

wherein R$^6$ is selected from the group consisting of C$_{1-8}$-alkyl, halogen, —NR$^e$R$^f$, and —NR$^c$C(O)R$^d$, R$^d$ is C$_{1-8}$-alkyl, and R$^e$ and R$^f$, at each occurrence, are independently selected from the group consisting of hydrogen and C$_{1-8}$-alkyl wherein r is 0, 1, 2, or 3 and R$^7$ is hydrogen, C$_{1-8}$-alkyl or, —C(O)C$_{1-8}$-alkyl.

Specific embodiments contemplated as part of the invention include, but are not limited to, compounds of formula (I), for example:

4-benzyl-6-(1H-pyrrolo[2,3-b]pyridin-3-yl)phthalazin-1 (2H)-one;
4-benzyl-6-(pyridin-4-yl)phthalazin-1(2H)-one;
4-benzyl-6-(1H-pyrazol-4-yl)phthalazin-1(2H)-one;
4-benzyl-6-(pyridin-3-yl)phthalazin-1(2H)-one;
4-(pyridin-4-ylmethyl)-6-(1H-pyrrolo[2,3-b]pyridin-3-yl) phthalazin-1(2H)-one;
4-(2,5-dichlorobenzyl)-6-(1H-pyrrolo[2,3-b]pyridin-3-yl) phthalazin-1(2H)-one;
4-(piperidin-3-ylmethyl)-6-(1H-pyrrolo[2,3-b]pyridin-3-yl)phthalazin-1(2H)-one;
4-(pyridin-3-ylmethyl)-6-(1H-pyrrolo[2,3-b]pyridin-3-yl) phthalazin-1(2H)-one;
4-(piperidin-4-ylmethyl)-6-(1H-pyrrolo[2,3-b]pyridin-3-yl)phthalazin-1(2H)-one;
4-(piperidin-2-ylmethyl)-6-(1H-pyrrolo[2,3-b]pyridin-3-yl)phthalazin-1(2H)-one;
4-[4-(dimethylamino)benzyl]-6-(1H-pyrrolo[2,3-b]pyridin-3-yl)phthalazin-1(2H)-one;
N-(4-{[4-oxo-7-(1H-pyrrolo[2,3-b]pyridin-3-yl)-3,4-dihydrophthalazin-1-yl]methyl}phenyl)acetamide; and
4-[(1-methyl-1H-pyrazol-3-yl)methyl]-6-(1H-pyrrolo [2,3-b]pyridin-3-yl)phthalazin-1(2H)-one.

Another aspect of the invention provides compounds of formula (II), wherein R$^{1a}$, R$^{1b}$, R$^{1c}$, and Z are as defined generally and in subsets above.

Formula (II)

In one aspect, the present invention provides compounds of formula (II), wherein R$^{1a}$, R$^{1b}$, and R$^{1c}$ are independently hydrogen, hydroxy, nitro, halogen, cyano, trifluoromethyl, trifluoromethoxy, C$_{1-4}$-alkyl, —OR$^a$, or —NR$^b$R$^c$;

Z is $C_{3-8}$-cycloalkyl, heterocycloalkyl, aryl, or heteroaryl, wherein the $C_{3-8}$-cycloalkyl, heterocycloalkyl, aryl, and heteroaryl are optionally substituted with one or more $R^6$;

$R^6$ is selected from the group consisting of $C_{1-8}$-alkyl, $C_{2-8}$-alkenyl, $C_{2-8}$-alkynyl, aryl, heterocyclyl, halogen, oxo, cyano, nitro, $-OR^d$, $-C(O)R^d$, $-C(O)OR^d$, $-OC(O)R^d$, $-NR^eR^f$, $-NR^eC(O)R^d$, $-NHC(O)NHR^e$, $-NHSO_2R^d$, $-C(O)NR^eR^f$, $-SR^d$, $-S(O)R^d$, $-SO_2R^d$, $-SO_2NR^eNR^f$, $-B(OH)_2$, $-CF_3$, $-CF_2CF_3$, $-OCF_3$, and $-OCF_2CF_3$ wherein (a) the $R^6$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, $-OR^g$, $-C(O)R^g$, $-C(O)OR^g$, $-OC(O)R^g$, $-NR^hR^i$, $-NR^hC(O)R^g$, $-NHSO_2R^g$, $-NHC(O)NHR^h$, $-C(O)NR^hR^i$; and wherein (b) the $R^6$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo $-OR^j$, $-C(O)R^j$, $-C(O)OR^j$, $-OC(O)R^j$, $-NR^kR^l$, $-NR^kC(O)R^j$, $-NHC(O)NHR^k$, $-NHSO_2R^j$, $-C(O)NR^kR^l$, $-SR^j$, $-S(O)R^j$, $-SO_2R^j$, $-SO_2NR^kNR^l$, $-CF_3$, $-CF_2CF_3$, $-OCF_3$, and $-OCF_2CF_3$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), $-O(C_{1-8}$-alkyl)$NH_2$, and $-N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$; wherein the aryl, aryl-($C_{1-8}$-alkyl)-, heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$;

$R^g$ at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$; and $R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$;

$R^k$ and $R^l$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^k$ and $R^l$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, $-NH_2$, $-NH(C_{1-8}$-alkyl), and $-N(C_{1-8}$-alkyl)$_2$;

or a pharmaceutically acceptable salt thereof.

In one embodiment of formula (II), $R^{1a}$, $R^{1b}$, and $R^{1c}$ are hydrogen. In another embodiment of formula (II), $R^{1b}$ and $R^{1c}$ are hydrogen and $R^{1a}$ is hydroxy, nitro, halogen, cyano, trifluoromethyl, trifluoromethoxy, $C_{1-4}$-alkyl, $-OR^a$, or $-NR^bR^c$. In another embodiment of formula (II), $R^{1a}$ and $R^{1c}$ are hydrogen and $R^{1b}$ is hydroxy, nitro, halogen, cyano, trifluoromethyl, trifluoromethoxy, $C_{1-4}$-alkyl, $-OR^a$, or $-NR^bR^c$. In another embodiment of formula (II), $R^{1a}$ and $R^{1b}$ are hydrogen and $R^{1c}$ is hydroxy, nitro, halogen, cyano, trifluoromethyl, trifluoromethoxy, $C_{1-4}$-alkyl, $-OR^a$, or $-NR^bR^c$.

In another embodiment of formula (II), Z is heterocycloalkyl, which is optionally substituted with one or more $R^6$. In another embodiment of formula (II), Z is heterocycloalkyl, which is substituted with one or more $R^6$. In another embodiment of formula (II), Z is heterocycloalkyl, which is unsubstituted. In another embodiment of formula (II), Z is tetrahydrofuranyl, tetrahydrothiophenyl, pyrrolidinyl, pyrazolidinyl, piperidinyl, or piperazinyl.

In another embodiment of formula (II), Z is aryl, which is optionally substituted with one or more $R^6$. In another embodiment of formula (II), Z is aryl, which is substituted with one or more $R^6$. In another embodiment of formula (II), Z is aryl, which is unsubstituted. In another embodiment of formula (II), Z is phenyl, naphthalenyl, or indenyl.

In another embodiment of formula (II), Z is heteroaryl, which is optionally substituted with one or more $R^6$. In another embodiment of formula (II), Z is heteroaryl, which is substituted with one or more $R^6$. In another embodiment of formula (II), Z is heteroaryl, which is unsubstituted. In another embodiment of formula (II), Z is furanyl, thiophenyl, pyrrolyl, imidazolyl, pyrazolyl, triazolyl, tetrazolyl, oxazolyl, isoxazolyl, thiazolyl, isothiazolyl, thiadiazolyl, oxadiazolyl, pyridinyl, pyrimidinyl, pyrazinyl, or triazinyl.

In another embodiment of formula (II), Z is selected from the group consisting of

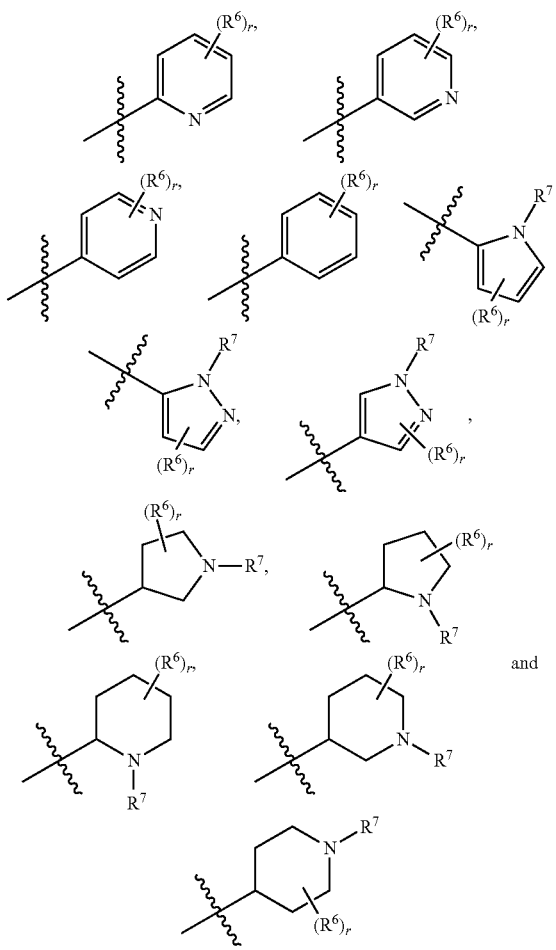

wherein $R^6$ is selected from the group consisting of $C_{1-8}$-alkyl, halogen, —$NR^eR^f$, and —$NR^eC(O)R^d$, $R^d$ is $C_{1-8}$-alkyl, and $R^e$ and $R^f$, at each occurrence, are independently selected from the group consisting of hydrogen and $C_{1-8}$-alkyl wherein r is 0, 1, 2, or 3 and $R^7$ is hydrogen, $C_{1-8}$-alkyl or , —$C(O)C_{1-8}$-alkyl.

Specific embodiments contemplated as part of the invention include, but are not limited to, compounds of formula (II), for example:

4-benzyl-6-(1H-pyrrolo[2,3-b]pyridin-3-yl)phthalazin-1(2H)-one;

4-(pyridin-4-ylmethyl)-6-(1H-pyrrolo[2,3-b]pyridin-3-yl)phthalazin-1(2H)-one;

4-(2,5-dichlorobenzyl)-6-(1H-pyrrolo[2,3-b]pyridin-3-yl)phthalazin-1(2H)-one;

4-(piperidin-3-ylmethyl)-6-(1H-pyrrolo[2,3-b]pyridin-3-yl)phthalazin-1(2H)-one;

4-(pyridin-3-ylmethyl)-6-(1H-pyrrolo[2,3-b]pyridin-3-yl)phthalazin-1(2H)-one;

4-(piperidin-4-ylmethyl)-6-(1H-pyrrolo[2,3-b]pyridin-3-yl)phthalazin-1(2H)-one;

4-(piperidin-2-ylmethyl)-6-(1H-pyrrolo[2,3-b]pyridin-3-yl)phthalazin-1(2H)-one;

4-[4-(dimethylamino)benzyl]-6-(1H-pyrrolo[2,3-b]pyridin-3-yl)phthalazin-1(2H)-one;

N-(4-{[4-oxo-7-(1H-pyrrolo[2,3-b]pyridin-3-yl)-3,4-dihydrophthalazin-1-yl]methyl}phenyl)acetamide; and 4-[(1-methyl-1H-pyrazol-3-yl)methyl]-6-(1H-pyrrolo[2,3-b]pyridin-3-yl)phthalazin-1(2H)-one.

Another aspect of the invention provides compounds of formula (III), wherein $R^{1a}$, $R^{1b}$, $R^{1c}$, and Z are as defined generally and in subsets above.

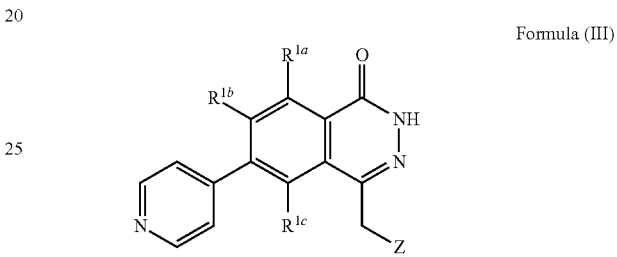

Formula (III)

In one aspect, the present invention provides compounds of formula (III),
wherein $R^{1a}$, $R^{1b}$, and $R^{1c}$ are independently hydrogen, hydroxy, nitro, halogen, cyano, trifluoromethyl, trifluoromethoxy, $C_{1-4}$-alkyl, —$OR^a$, or —$NR^bR^c$;

Z is $C_{3-8}$-cycloalkyl, heterocycloalkyl, aryl, or heteroaryl, wherein the $C_{3-8}$-cycloalkyl, heterocycloalkyl, aryl, and heteroaryl are optionally substituted with one or more $R^6$;

$R^6$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^d$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^6$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^g$, —$C(O)R^g$, —$C(O)OR^g$, —$OC(O)R^g$, —$NR^hR^i$, —$NR^hC(O)R^g$, —$NHSO_2R^g$, —$NHC(O)NHR^h$, —$C(O)NR^hR^i$; and wherein (b) the $R^6$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^j$, —$C(O)R^j$, —$C(O)OR^j$, —$OC(O)R^j$, —$NR^kR^l$, —$NR^kC(O)R^j$, —$NHC(O)NHR^k$, —$NHSO_2R^j$, —$C(O)NR^kR^l$, —$SR^j$, —$S(O)R^j$, —$SO_2R^j$, —$SO_2NR^kNR^l$, —$CF_3$, —$CF_2CF_3$, —$OCF_3$, and —$OCF_2CF_3$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), —$O(C_{1-8}$-alkyl)$NH_2$, and —$N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$; wherein the aryl, aryl-($C_{1-8}$-alkyl)-, heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$; and $R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^k$ and $R^l$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^k$ and $R^l$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

In one embodiment of formula (III), $R^{1a}$, $R^{1b}$, and $R^{1c}$ are hydrogen. In another embodiment of formula (III), $R^{1b}$ and $R^{1c}$ are hydrogen and $R^{1a}$ is hydroxy, nitro, halogen, cyano, trifluoromethyl, trifluoromethoxy, $C_{1-4}$-alkyl, —$OR^a$, or —$NR^bR^c$. In another embodiment of formula (III), $R^{1a}$ and $R^{1c}$ are hydrogen and $R^{1b}$ is hydroxy, nitro, halogen, cyano, trifluoromethyl, trifluoromethoxy, $C_{1-4}$-alkyl, —$OR^a$, or —$NR^bR^c$. In another embodiment of formula (III), $R^{1a}$ and $R^{1b}$ are hydrogen and $R^{1c}$ is hydroxy, nitro, halogen, cyano, trifluoromethyl, trifluoromethoxy, $C_{1-4}$-alkyl, —$OR^a$, or —$NR^bR^c$.

In another embodiment of formula (III), Z is heterocycloalkyl, which is optionally substituted with one or more $R^6$. In another embodiment of formula (III), Z is heterocycloalkyl, which is substituted with one or more $R^6$. In another embodiment of formula (III), Z is heterocycloalkyl, which is unsubstituted. In another embodiment of formula (III), Z is tetrahydrofuranyl, tetrahydrothiophenyl, pyrrolidinyl, pyrazolidinyl, piperidinyl, or piperazinyl.

In another embodiment of formula (III), Z is aryl, which is optionally substituted with one or more $R^6$. In another embodiment of formula (III), Z is aryl, which is substituted with one or more $R^6$. In another embodiment of formula (III), Z is aryl, which is unsubstituted. In another embodiment of formula (III), Z is phenyl, naphthalenyl, or indenyl.

In another embodiment of formula (III), Z is heteroaryl, which is optionally substituted with one or more $R^6$. In another embodiment of formula (III), Z is heteroaryl, which is substituted with one or more $R^6$. In another embodiment of formula (III), Z is heteroaryl, which is unsubstituted. In another embodiment of formula (III), Z is furanyl, thiophenyl, pyrrolyl, imidazolyl, pyrazolyl, triazolyl, tetrazolyl, oxazolyl, isoxazolyl, thiazolyl, isothiazolyl, thiadiazolyl, oxadiazolyl, pyridinyl, pyrimidinyl, pyrazinyl, or triazinyl.

In another embodiment of formula (III), Z is selected from the group consisting of

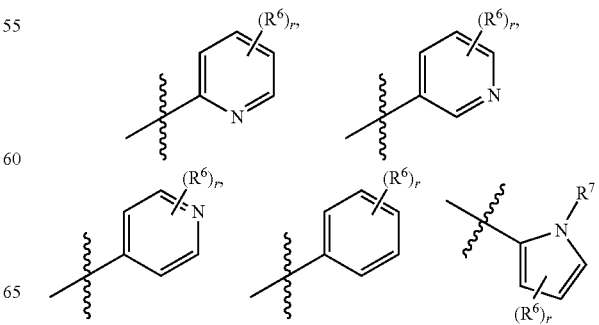

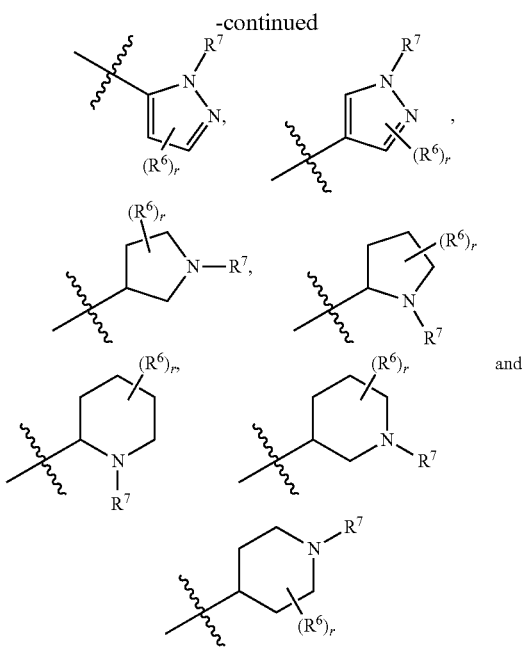

wherein R⁶ is selected from the group consisting of $C_{1-8}$-alkyl, halogen, —NR$^e$R$^f$, and —NR$^e$C(O)R$^d$, R$^d$ is $C_{1-8}$-alkyl, and R$^e$ and R$^f$, at each occurrence, are independently selected from the group consisting of hydrogen and $C_{1-8}$-alkyl wherein r is 0, 1, 2, or 3 and R⁷ is hydrogen, $C_{1-8}$-alkyl or , —C(O)$C_{1-8}$-alkyl.

Specific embodiments contemplated as part of the invention include, but are not limited to, compounds of formula (III), for example:

4-benzyl-6-(pyridin-4-yl)phthalazin-1(2H)-one.

Another aspect of the invention provides compounds of formula (IV), wherein R$^{1a}$, R$^{1b}$, R$^{1c}$, and Z are as defined generally and in subsets above.

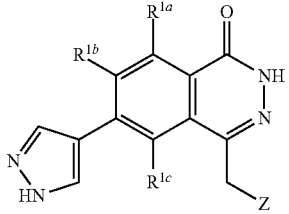

Formula (IV)

In one aspect, the present invention provides compounds of formula (IV), wherein R$^{1a}$, R$^{1b}$, and R$^{1c}$ are independently hydrogen, hydroxy, nitro, halogen, cyano, trifluoromethyl, trifluoromethoxy, $C_{1-4}$-alkyl, —OR$^a$, or —NR$^b$R$^c$;

Z is $C_{3-8}$-cycloalkyl, heterocycloalkyl, aryl, or heteroaryl, wherein the $C_{3-8}$-cycloalkyl, heterocycloalkyl, aryl, and heteroaryl are optionally substituted with one or more R⁶;

R⁶ is selected from the group consisting of $C_{1-8}$-alkyl, $C_{2-8}$-alkenyl, $C_{2-8}$-alkynyl, aryl, heterocyclyl, halogen, oxo, cyano, nitro, —OR$^d$, —C(O)R$^d$, —C(O)OR$^d$, —OC(O)R$^d$, —NR$^e$R$^f$, —NR$^e$C(O)R$^d$, —NHC(O)NHR$^e$, —NHSO$_2$R$^d$, —C(O)NR$^e$R$^f$, —SR$^d$, —S(O)R$^d$, —SO$_2$R$^d$, —SO$_2$NR$^e$NR$^f$, —B(OH)$_2$, —CF$_3$, —CF$_2$CF$_3$, —OCF$_3$, and —OCF$_2$CF$_3$ wherein (a) the R⁶ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —OR$^g$, —C(O)R$^g$, —C(O)OR$^g$, —OC(O)R$^g$, —NR$^h$R$^i$, —NR$^h$C(O) R$^g$, —NHSO$_2$R$^g$, —NHC(O)NHR$^h$, —C(O)NR$^h$R$^i$; and wherein (b) the R⁶ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —OR$^j$, —C(O)R$^j$, —C(O)OR$^j$, —OC(O)R$^j$, —NR$^k$R$^l$, —NR$^k$C(O)R$^j$, —NHC(O)NHR$^k$, —NHSO$_2$R$^j$, —C(O)NR$^k$R$^l$, —SR$^j$, —S(O)R$^j$, —SO$_2$R$^j$, —SO$_2$NR$^k$NR$^l$, —CF$_3$, —CF$_2$CF$_3$, —OCF$_3$, and —OCF$_2$CF$_3$;

R$^a$, at each occurrence, is selected from the group consisting of hydrogen, $C_{1-8}$-alkyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —NH$_2$, —NH($C_{1-8}$-alkyl), —O($C_{1-8}$-alkyl)NH$_2$, and —N($C_{1-8}$-alkyl)$_2$;

R$^b$ and R$^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, R$^b$ and R$^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —NH$_2$, —NH($C_{1-8}$-alkyl), and —N($C_{1-8}$-alkyl)$_2$;

R$^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, oxo, hydroxy, $C_{1-8}$-alkoxy, —NH$_2$, —NH($C_{1-8}$-alkyl), and —N($C_{1-8}$-alkyl)$_2$; wherein the aryl, aryl-($C_{1-8}$-alkyl)-, heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —NH$_2$, —NH($C_{1-8}$-alkyl), and —N($C_{1-8}$-alkyl)$_2$;

R$^e$ and R$^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, R$^e$ and R$^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —NH$_2$, —NH($C_{1-8}$-alkyl), and —N($C_{1-8}$-alkyl)$_2$;

R$^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —NH$_2$, —NH($C_{1-8}$-alkyl), and —N($C_{1-8}$-alkyl)$_2$; and $R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^k$ and $R^l$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^k$ and $R^l$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

In one embodiment of formula (IV), $R^{1a}$, $R^{1b}$, and $R^{1c}$ are hydrogen. In another embodiment of formula (IV), $R^{1b}$ and $R^{1c}$ are hydrogen and $R^{1a}$ is hydroxy, nitro, halogen, cyano, trifluoromethyl, trifluoromethoxy, $C_{1-4}$-alkyl, —$OR^a$, or —$NR^bR^c$. In another embodiment of formula (IV), $R^{1a}$ and $R^{1c}$ are hydrogen and $R^{1b}$ is hydroxy, nitro, halogen, cyano, trifluoromethyl, trifluoromethoxy, $C_{1-4}$-alkyl, —$OR^a$, or —$NR^bR^c$. In another embodiment of formula (IV), $R^{1a}$ and $R^{1b}$ are hydrogen and $R^{1c}$ is hydroxy, nitro, halogen, cyano, trifluoromethyl, trifluoromethoxy, $C_{1-4}$-alkyl, —$OR^a$, or —$NR^bR^c$.

In another embodiment of formula (IV), Z is heterocycloalkyl, which is optionally substituted with one or more $R^6$. In another embodiment of formula (IV), Z is heterocycloalkyl, which is substituted with one or more $R^6$. In another embodiment of formula (IV), Z is heterocycloalkyl, which is unsubstituted. In another embodiment of formula (IV), Z is tetrahydrofuranyl, tetrahydrothiophenyl, pyrrolidinyl, pyrazolidinyl, piperidinyl, or piperazinyl.

In another embodiment of formula (IV), Z is aryl, which is optionally substituted with one or more $R^6$. In another embodiment of formula (IV), Z is aryl, which is substituted with one or more $R^6$. In another embodiment of formula (IV), Z is aryl, which is unsubstituted. In another embodiment of formula (IV), Z is phenyl, naphthalenyl, or indenyl.

In another embodiment of formula (IV), Z is heteroaryl, which is optionally substituted with one or more $R^6$. In another embodiment of formula (IV), Z is heteroaryl, which is substituted with one or more $R^6$. In another embodiment of formula (IV), Z is heteroaryl, which is unsubstituted. In another embodiment of formula (IV), Z is furanyl, thiophenyl, pyrrolyl, imidazolyl, pyrazolyl, triazolyl, tetrazolyl, oxazolyl, isoxazolyl, thiazolyl, isothiazolyl, thiadiazolyl, oxadiazolyl, pyridinyl, pyrimidinyl, pyrazinyl, or triazinyl.

In another embodiment of formula (IV), Z is selected from the group consisting of

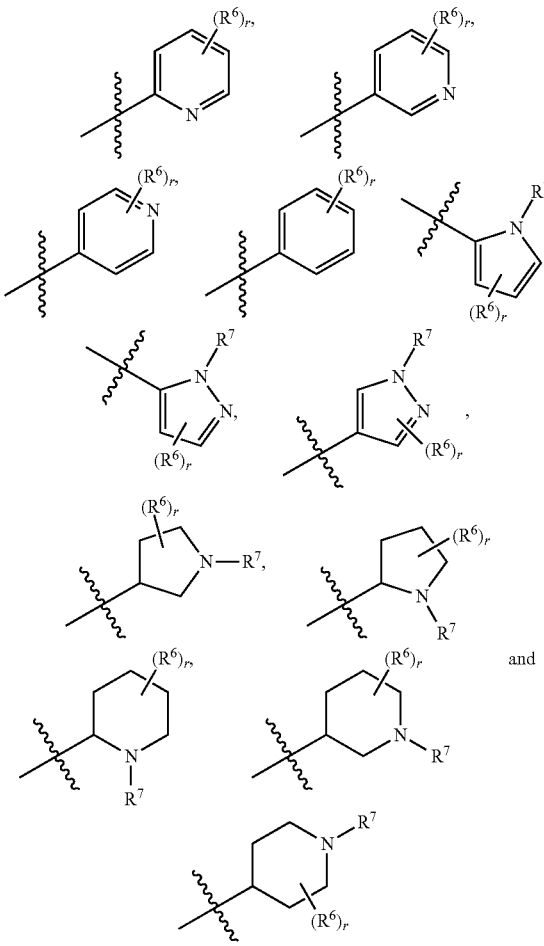

wherein $R^6$ is selected from the group consisting of $C_{1-8}$-alkyl, halogen, —$NR^eR^f$, and —$NR^eC(O)R^d$, $R^d$ is $C_{1-8}$-alkyl, and $R^e$ and $R^f$, at each occurrence, are independently selected from the group consisting of hydrogen and $C_{1-8}$-alkyl wherein r is 0, 1, 2, or 3 and $R^7$ is hydrogen, $C_{1-8}$-alkyl or , —$C(O)C_{1-8}$-alkyl.

Specific embodiments contemplated as part of the invention include, but are not limited to, compounds of formula (IV), for example:

4-benzyl-6-(1H-pyrazol-4-yl)phthalazin-1(2H)-one.

Another aspect of the invention provides compounds of formula (V), wherein $R^{1a}$, $R^{1b}$, $R^{1c}$, and Z are as defined generally and in subsets above.

Formula (V)

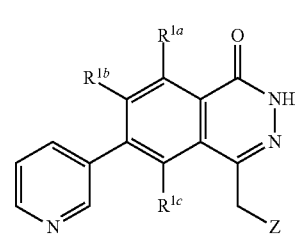

In one aspect, the present invention provides compounds of formula (V), wherein $R^{1a}$, $R^{1b}$, and $R^{1c}$ are independently hydrogen, hydroxy, nitro, halogen, cyano, trifluoromethyl, trifluoromethoxy, $C_{1-4}$-alkyl, —$OR^a$, or —$NR^bR^c$;

Z is $C_{3-8}$-cycloalkyl, heterocycloalkyl, aryl, or heteroaryl, wherein the $C_{3-8}$-cycloalkyl, heterocycloalkyl, aryl, and heteroaryl are optionally substituted with one or more $R^6$;

$R^6$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^d$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^6$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^g$, —$C(O)R^g$, —$C(O)OR^g$, —$OC(O)R^g$, —$NR^hR^i$, —$NR^hC(O)R^g$, —$NHSO_2R^g$, —$NHC(O)NHR^h$, —$C(O)NR^hR^i$; and wherein (b) the $R^6$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^j$, —$C(O)R^j$, —$C(O)OR^j$, —$OC(O)R^j$, —$NR^kR^l$, —$NR^kC(O)R^j$, —$NHC(O)NHR^k$, —$NHSO_2R^j$, —$C(O)NR^kR^l$, —$SR^j$, —$S(O)R^j$, —$SO_2R^j$, —$SO_2NR^kNR^l$, —$CF_3$, —$CF_2CF_3$, —$OCF_3$, and —$OCF_2CF_3$;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), —$O(C_{1-8}$-alkyl)$NH_2$, and —$N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$; wherein the aryl, aryl-($C_{1-8}$-alkyl)-, heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —NH($C_{1-8}$-alkyl), and —$N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^g$ at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$; and $R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-allcynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-allcynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^k$ and $R^l$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^k$ and $R^l$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

In one embodiment of formula (V), $R^{1a}$, $R^{1b}$, and $R^{1c}$ are hydrogen. In another embodiment of formula (V), $R^{1b}$ and $R^{1c}$ are hydrogen and $R^{1a}$ is hydroxy, nitro, halogen, cyano, trifluoromethyl, trifluoromethoxy, $C_{1-4}$-alkyl, —$OR^a$, or —$NR^bR^c$. In another embodiment of formula (V), $R^{1a}$ and $R^{1c}$ are hydrogen and $R^{1b}$ is hydroxy, nitro, halogen, cyano, trifluoromethyl, trifluoromethoxy, $C_{1-4}$-alkyl, —$OR^a$, or —$NR^bR^c$. In another embodiment of formula (V), $R^{1a}$ and $R^{1b}$ are hydrogen and $R^{1c}$ is hydroxy, nitro, halogen, cyano, trifluoromethyl, trifluoromethoxy, $C_{1-4}$-alkyl, —$OR^a$, or —$NR^bR^c$.

In one embodiment of formula (V), $R^{1a}$, $R^{1b}$, and $R^{1c}$ are hydrogen. In another embodiment of formula (V), $R^{1b}$ and $R^{1c}$ are hydrogen and $R^{1a}$ is hydroxy, nitro, halogen, cyano, trifluoromethyl, trifluoromethoxy, $C_{1-4}$-alkyl, —$OR^a$, or —$NR^bR^c$. In another embodiment of formula (V), $R^{1a}$ and $R^{1c}$ are hydrogen and $R^{1b}$ is hydroxy, nitro, halogen, cyano, trifluoromethyl, trifluoromethoxy, $C_{1-4}$-alkyl, —$OR^a$, or —$NR^bR^c$. In another embodiment of formula (V), $R^{1a}$ and $R^{1b}$ are hydrogen and $R^{1c}$ is hydroxy, nitro, halogen, cyano, trifluoromethyl, trifluoromethoxy, $C_{1-4}$-alkyl, —$OR^a$, or —$NR^bR^c$.

In another embodiment of formula (V), Z is heterocycloalkyl, which is optionally substituted with one or more $R^6$. In another embodiment of formula (V), Z is heterocycloalkyl, which is substituted with one or more $R^6$. In another embodiment of formula (V), Z is heterocycloalkyl, which is unsubstituted. In another embodiment of formula (V), Z is tetrahydrofuranyl, tetrahydrothiophenyl, pyrrolidinyl, pyrazolidinyl, piperidinyl, or piperazinyl.

In another embodiment of formula (V), Z is aryl, which is optionally substituted with one or more $R^6$. In another embodiment of formula (V), Z is aryl, which is substituted with one or more $R^6$. In another embodiment of formula (V), Z is aryl, which is unsubstituted. In another embodiment of formula (V), Z is phenyl, naphthalenyl, or indenyl.

In another embodiment of formula (V), Z is heteroaryl, which is optionally substituted with one or more $R^6$. In another embodiment of formula (V), Z is heteroaryl, which is substituted with one or more $R^6$. In another embodiment of formula (V), Z is heteroaryl, which is unsubstituted. In another embodiment of formula (V), Z is furanyl, thiophenyl, pyrrolyl, imidazolyl, pyrazolyl, triazolyl, tetrazolyl, oxazolyl, isoxazolyl, thiazolyl, isothiazolyl, thiadiazolyl, oxadiazolyl, pyridinyl, pyrimidinyl, pyrazinyl, or triazinyl.

In another embodiment of formula (V), Z is selected from the group consisting of

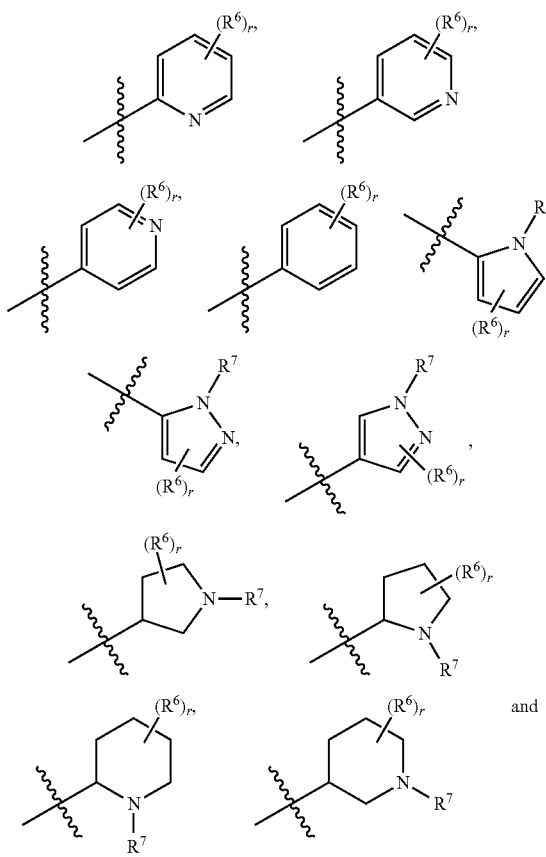

and

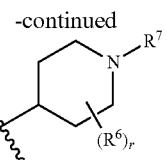

wherein $R^6$ is selected from the group consisting of $C_{1-8}$-alkyl, halogen, —$NR^eR^f$, and —$NR^eC(O)R^d$, $R^d$ is $C_{1-8}$-alkyl, and $R^e$ and $R^f$, at each occurrence, are independently selected from the group consisting of hydrogen and $C_{1-8}$-alkyl wherein r is 0, 1, 2, or 3 and $R^7$ is hydrogen, $C_{1-8}$-alkyl or, —$C(O)C_{1-8}$-alkyl.

Specific embodiments contemplated as part of the invention include, but are not limited to, compounds of formula (V), for example:
4-benzyl-6-(pyridin-3-yl)phthalazin-1(2H)-one.

Compounds of this invention may contain asymmetrically substituted carbon atoms in the R or S configuration, wherein the terms "R" and "S" are as defined in Pure Appl. Chem. (1976) 45, 13-10. Compounds having asymmetrically substituted carbon atoms with equal amounts of R and S configurations are racemic at those atoms. Atoms having excess of one configuration over the other are assigned the configuration in excess, preferably an excess of about 85%-90%, more preferably an excess of about 95%-99%, and still more preferably an excess greater than about 99%. Accordingly, this invention is meant to embrace racemic mixtures and relative and absolute diastereoisomers of the compounds thereof.

Compounds of this invention may also contain carbon-carbon double bonds or carbon-nitrogen double bonds in the E or Z configuration, wherein the term "E" represents higher order substituents on opposite sides of the carbon-carbon or carbon-nitrogen double bond and the term "Z" represents higher order substituents on the same side of the carbon-carbon or carbon-nitrogen double bond as determined by the Cahn-Ingold-Prelog Priority Rules. The compounds of this invention may also exist as a mixture of "E" and "Z" isomers.

Additional geometric isomers may exist in the present compounds. For example, the invention contemplates the various geometric isomers and mixtures thereof resulting from the disposition of substituents around a cycloalkyl group or a heterocycle group. Substituents around a cycloalkyl or a heterocycle are designated as being of cis or trans configuration.

Compounds of this invention may also exist as tautomers or equilibrium mixtures thereof wherein a proton of a compound shifts from one atom to another. Examples of tautomers include, but are not limited to, keto-enol, phenol-keto, oxime-nitroso, nitro-aci, imine-enamine and the like. Tautomeric forms are intended to be encompassed by the scope of this invention, even though only one tautomeric form may be depicted.

This invention also is directed, in part, to all salts of the compounds of formula (I). A salt of a compound may be advantageous due to one or more of the salt's properties, such as, for example, enhanced pharmaceutical stability in differing temperatures and humidities, or a desirable solubility in water or other solvents. Where a salt is intended to be administered to a patient (as opposed to, for example, being in use in an in vitro context), the salt preferably is pharmaceutically acceptable and/or physiologically compatible. The term "pharmaceutically acceptable" is used adjectivally in this patent application to mean that the modified noun is appropriate for use as a pharmaceutical product or as a part of a pharmaceutical product. Pharmaceutically acceptable salts include salts commonly used to form alkali metal salts and to form addition salts of free acids or free bases. In general, these salts typically may be prepared by conventional means by reacting, for example, the appropriate acid or base with a compound of the invention.

Pharmaceutically acceptable acid addition salts of the compounds of formula (I) can be prepared from an inorganic or organic acid. Examples of often suitable inorganic acids include hydrochloric, hydrobromic, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of often suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, beta-hydroxybutyric acid, galactarate, galacturonate, adipate, alginate, bisulfate, butyrate, camphorate, camphorsulfonate, cyclopentanepropionate, dodecylsulfate, glycoheptanoate, glycerophosphate, heptanoate, hexanoate, nicotinate, oxalate, palmoate, pectinate, 2-naphthalesulfonate, 3-phenylpropionate, picrate, pivalate, thiocyanate, tosylate, and undecanoate.

Pharmaceutically acceptable base addition salts of the compounds of formula (I) include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl ($C_1$-$C_6$) halides (e.g., methyl, ethyl, propyl, and butyl chlorides, bromides, and iodides), dialkyl sulfates (e.g., dimethyl, diethyl, dibutyl, and diamyl sulfates), long chain halides (e.g., decyl, lauryl, myristyl, and stearyl chlorides, bromides, and iodides), arylalkyl halides (e.g., benzyl and phenethyl bromides), and others.

Compounds of formula (I) (and salts thereof) with any level of purity (including pure and substantially pure) are within the scope of Applicants' invention. The term "substantially pure" in reference to a compound/salt/isomer, means that the preparation/composition containing the compound/salt/isomer contains more than about 85% by weight of the compound/salt/isomer, preferably more than about 90% by weight of the compound/salt/isomer, preferably more than about 95% by weight of the compound/salt/isomer, preferably more than about 97% by weight of the compound/salt/isomer, and preferably more than about 99% by weight of the compound/salt/isomer.

Preparation of Compounds

Compounds of this invention may be made by synthetic chemical processes, examples of which are shown herein. It is meant to be understood that the order of the steps in the processes may be varied, that reagents, solvents and reaction conditions may be substituted for those specifically mentioned, and that vulnerable moieties may be protected and deprotected, as necessary.

Protecting groups for C(O)OH moieties include, but are not limited to, acetoxymethyl, allyl, benzoylmethyl, benzyl, benzyloxymethyl, tert-butyl, tert-butyldiphenylsilyl, diphenylmethyl, cyclobutyl, cyclohexyl, cyclopentyl, cyclopropyl, diphenylmethylsilyl, ethyl, para-methoxybenzyl, methoxymethyl, methoxyethoxymethyl, methyl, methylthiomethyl, naphthyl, para-nitrobenzyl, phenyl, n-propyl, 2,2,2-trichloroethyl, triethylsilyl, 2-(trimethylsilyl)ethyl, 2-(trimethylsilyl)ethoxymethyl, triphenylmethyl and the like. Protecting groups for C(O) and C(O)H moieties include, but are not limited to, 1,3-dioxylketal, diethylketal, dimethylketal, 1,3-dithianylketal, O-methyloxime, O-phenyloxime and the like.

Protecting groups for NH moieties include, but are not limited to, acetyl, alanyl, benzoyl, benzyl(phenylmethyl), benzylidene, benzyloxycarbonyl (Cbz), tert-butoxycarbonyl (Boc), 3,4-dimethoxybenzyloxycarbonyl, diphenylmethyl, diphenylphosphoryl, formyl, methanesulfonyl, para-methoxybenzyloxycarbonyl, phenylacetyl, phthaloyl, succinyl, trichloroethoxycarbonyl, triethylsilyl, trifluoroacetyl, trimethylsilyl, triphenylmethyl, triphenylsilyl, para-toluenesulfonyl and the like.

Protecting groups for OH and SH moieties include, but are not limited to, acetyl, allyl, allyloxycarbonyl, benzyloxycarbonyl (Cbz), benzoyl, benzyl, tert-butyl, tert-butyldimethylsilyl, tert-butyldiphenylsilyl, 3,4-dimethoxybenzyl, 3,4-dimethoxybenzyloxycarbonyl, 1,1-dimethyl-2-propenyl, diphenylmethyl, formyl, methanesulfonyl, methoxyacetyl, 4-methoxybenzyloxycarbonyl, para-methoxybenzyl, methoxycarbonyl, methyl, para-toluenesulfonyl, 2,2,2-trichloroethoxycarbonyl, 2,2,2-trichloroethyl, triethylsilyl, trifluoroacetyl, 2-(trimethylsilyl)ethoxycarbonyl, 2-trimethylsilylethyl, triphenylmethyl, 2-(triphenylphosphonio)ethoxycarbonyl and the like.

The present compounds may be prepared by a variety of processes well known for the preparation of compounds of this class. For example, the compounds of formula (I) wherein the groups X, Y, $R^{1a}$, $R^{1b}$, and $R^{1c}$ have the meanings as set forth in the summary unless otherwise noted, can be synthesized according to the general methods described in Schemes 1-5, using appropriate starting materials by methods generally available to one of ordinary skill in the art.

Abbreviations which have been used in the descriptions of the Schemes and the Examples that follow are: DMF for N,N-dimethylformamide, DMSO for dimethyl sulfoxide, DMSO-$d_6$ for deuteriated dimethyl sulfoxide, DME for dimethoxyethane, dppf for 1,1'-bis(diphenylphosphino)ferrocene, $Et_2O$ for diethyl ether, EtOAc for ethyl acetate, $Et_3N$ for triethylamine, Ts for toluene sulfonyl, and THF for tetrahydrofuran.

Schemes

Scheme 1

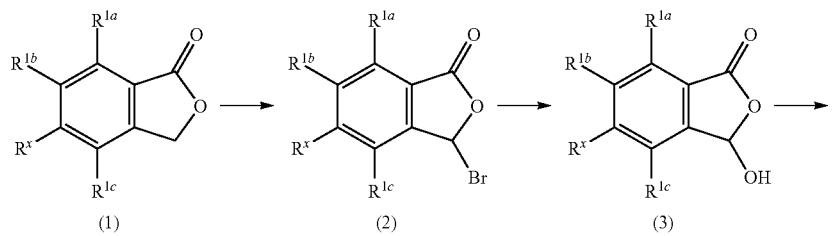

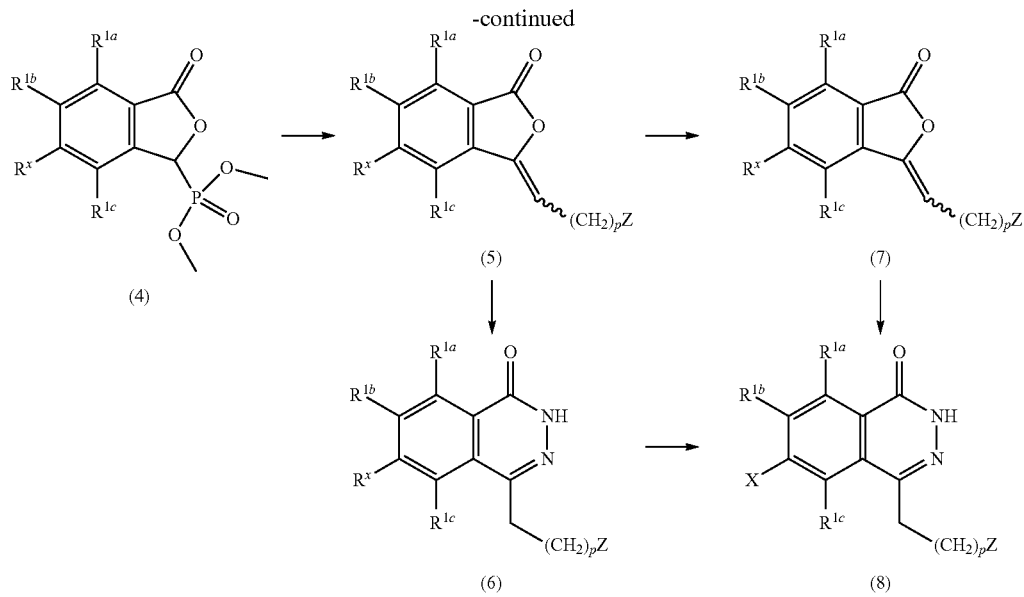

-continued (4) (5) (7)

(6) (8)

As shown in scheme 1, compounds of formula (1), wherein $R^{1a}$, $R^{1b}$, and $R^{1c}$ are as described herein and $R^x$ is a halogen or triflate, can be reacted with N-bromosuccinimide in the presence of a catalyst such as but not limited to benzoyl peroxide, to provide compounds of formula (2). The reaction is typically performed at an elevated temperature in an anhydrous solvent such as but not limited to carbon tetrachloride. Compounds of formula (3) can be prepared from compounds of formula (2) by reacting the latter with an aqueous base such as but not limited to aqueous potassium hydroxide. The reaction may require an elevated temperature. Compounds of formula (3) can be reacted with dimethyl phosphite in the presence of a base such as but not limited to sodium methoxide to provide compounds of formula (4). The addition is typically performed in a solvent such as but not limited to methanol at reduced temperature before allowing the reaction to warm to ambient temperature. Compounds of formula (4) can be reacted with compounds of formula $Z—(CH_2)_pC(O)$ H, wherein Z is a substituted or unsubstituted $C_{3-8}$-cycloalkyl, heterocycloalkyl, aryl, or heteroaryl, and p is 0, 1, or 2, and a base such as but not limited to triethylamine to provide compounds of formula (5). The reaction is typically performed in a solvent such as but not limited to tetrahydrofuran at ambient temperature. Compounds of formula (5) can be reacted with a boronic acid $(X—B(OH)_2)$ or a boron-ester wherein X is heteroaryl, to provide compounds of formula (7). The reaction is typically performed in the presence of a palladium catalyst and a base at elevated temperature (e.g. at about 70° C. to about 150° C. or optionally under microwave irradiation) and in a suitable solvent such as DMF, dioxane, ethanol, water, DME, or mixtures thereof. Non-limiting examples of suitable palladium catalysts include dichlorobis (triphenylphosphine)palladium(II), $PdCl_2(dppf)_2$, and tetrakis(triphenylphosphine)palladium. Suitable bases include, but are not limited to, cesium fluoride, sodium carbonate, potassium acetate, cesium carbonate. Compounds of formula (7) can be reacted with hydrazine in a suitable solvent such as but not limited to ethanol, to provide compounds of formula (8), which are representative of the compounds of this invention.

Alternatively, compounds of formula (5) can be reacted with hydrazine in a suitable solvent such as but not limited to ethanol, to provide compounds of formula (6), followed by reacting compounds of formula (6) under the Suzuki coupling conditions described above to provide compounds of formula (8), which are representative of the compounds of this invention.

Unless otherwise noted, microwave reactions described herein were carried out either in a Biotage Initiator 8 or in a CEM Explorer at 200 W. All reverse-phase HPLC purifications were carried out using a Zorbax C-18, 250×2.54 column and a eluting with a 0-100% gradient of mobile phase A (0.1% trifluoroacetic acid (TFA) in water) and mobile phase B (0.1% TFA in $CH_3CN$).

Compositions

In another aspect, the present invention provides pharmaceutical compositions for modulating kinase activity in a humans and animals that will typically contain a compound of formula (I) and a pharmaceutically acceptable carrier.

Compounds having formula (I) may be administered, for example, bucally, ophthalmically, orally, osmotically, parenterally (intramuscularly, intraperintoneally intrasternally, intravenously, subcutaneously), rectally, topically, transdermally, vaginally and intraarterially as well as by intraarticular injection, infusion, and placement in the body, such as, for example, the vasculature.

Compounds having formula (I) may be administered with or without an excipient. Excipients include, but are not limited to, encapsulators and additives such as absorption accelerators, antioxidants, binders, buffers, coating agents, coloring agents, diluents, disintegrating agents, emulsifiers, extenders, fillers, flavoring agents, humectants, lubricants, perfumes, preservatives, propellants, releasing agents, sterilizing agents, sweeteners, solubilizers, wetting agents, mixtures thereof and the like.

Excipients for preparation of compositions comprising a compound having formula (I) to be administered orally include, but are not limited to, agar, alginic acid, aluminum hydroxide, benzyl alcohol, benzyl benzoate, 1,3-butylene glycol, carbomers, castor oil, cellulose, cellulose acetate, cocoa butter, corn starch, corn oil, cottonseed oil, cross-povidone, diglycerides, ethanol, ethyl cellulose, ethyl laureate, ethyl oleate, fatty acid esters, gelatin, germ oil, glucose, glycerol, groundnut oil, hydroxypropylmethyl celluose, isopropanol, isotonic saline, lactose, magnesium hydroxide, magnesium stearate, malt, mannitol, monoglycerides, olive oil, peanut oil, potassium phosphate salts, potato starch, povidone, propylene glycol, Ringer's solution, safflower oil, sesame oil, sodium carboxymethyl cellulose, sodium phosphate salts, sodium lauryl sulfate, sodium sorbitol, soybean oil, stearic acids, stearyl fumarate, sucrose, surfactants, talc, tragacanth, tetrahydrofurfuryl alcohol, triglycerides, water, mixtures thereof and the like. Excipients for preparation of compositions comprising a compound having formula (I) to be administered ophthalmically or orally include, but are not limited to, 1,3-butylene glycol, castor oil, corn oil, cottonseed oil, ethanol, fatty acid esters of sorbitan, germ oil, groundnut oil, glycerol, isopropanol, olive oil, polyethylene glycols, propylene glycol, sesame oil, water, mixtures thereof and the like. Excipients for preparation of compositions comprising a compound having formula (I) to be administered osmotically include, but are not limited to, chlorofluorohydrocarbons, ethanol, water, mixtures thereof and the like. Excipients for preparation of compositions comprising a compound having formula (I) to be administered parenterally include, but are not limited to, 1,3-butanediol, castor oil, corn oil, cottonseed oil, dextrose, germ oil, groundnut oil, liposomes, oleic acid, olive oil, peanut oil, Ringer's solution, safflower oil, sesame oil, soybean oil, U.S.P. or isotonic sodium chloride solution, water, mixtures thereof and the like. Excipients for preparation of compositions comprising a compound having formula (I) to be administered rectally or vaginally include, but are not limited to, cocoa butter, polyethylene glycol, wax, mixtures thereof and the like.

The pharmaceutical composition and the method of the present invention may further comprise other therapeutically active compounds as noted herein which are usually applied in the treatment of the above-mentioned pathological conditions.

Methods of Use

In another aspect, the present invention provides methods of using a compound or composition of the invention to treat or prevent a disease or condition involving mediation, overexpression or disregulation of kinases in a mammal In particular, compounds of this invention are expected to have utility in treatment of diseases or conditions during which protein kinases such as any or all CDC-7 family members are expressed.

In one group of embodiments, diseases and conditions of humans or other animals that can be treated with inhibitors of kinases, include, but are not limited to, acoustic neuroma, acute leukemia, acute lymphocytic leukemia, acute myelocytic leukemia (monocytic, myeloblastic, adenocarcinoma, angiosarcoma, astrocytoma, myelomonocytic and promyelocytic), acute t-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic (granulocytic) leukemia, chronic myeleogeneous leukemia, colon cancer, colorectal cancer, craniopharyngioma, cystadenocarcinoma, diffuse large B-cell lymphoma, dysproliferative changes (dysplasias and metaplasias), embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, heavy chain disease, hemangioblastoma, hepatoma, hepatocellular cancer, hormone insensitive prostate cancer, leiomyosarcoma, liposarcoma, lung cancer, lymphagioendotheliosarcoma, lymphangiosarcoma, lymphoblastic leukemia, lymphoma (Hodgkin's and non-Hodgkin's), malignancies and hyperproliferative disorders of the bladder, breast, colon, lung, ovaries, pancreas, prostate, skin and uterus, lymphoid malignancies of T-cell or B-cell origin, leukemia, lymphoma, medullary carcinoma, medulloblastoma, melanoma, meningioma, mesothelioma, multiple myeloma, myelogenous leukemia, myeloma, myxosarcoma, neuroblastoma, non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer and Wilms' tumor.

The methods of the present invention typically involve administering to a subject in need of therapeutic treatment an effective amount of a compound of formula (I). Therapeutically effective amounts of a compound having formula (I) depend on recipient of treatment, disease treated and severity thereof, composition comprising it, time of administration, route of administration, duration of treatment, potency, rate of clearance and whether or not another drug is co-administered. The amount of a compound having formula (I) used to make a composition to be administered daily to a patient in a single dose or in divided doses is from about 0.03 to about 200 mg/kg body weight. Single dose compositions contain these amounts or a combination of submultiples thereof.

Combination Therapy

The present invention further provides methods of using a compound or composition of the invention in combination with one or more additional active agents.

Compounds having Formula (I) are expected to be useful when used with alkylating agents, angiogenesis inhibitors, antibodies, antimetabolites, antimitotics, antiproliferatives, antivirals, aurora kinase inhibitors, apoptosis promoters (for example, Bcl-xL, Bcl-w and Bfl-1) inhibitors, activators of death receptor pathway, Bcr-Abl kinase inhibitors, BiTE (Bi-Specific T cell Engager) antibodies, antibody drug conjugates, biologic response modifiers, cyclin-dependent kinase inhibitors, cell cycle inhibitors, cyclooxygenase-2 inhibitors, DVDs, leukemia viral oncogene homolog (ErbB2) receptor inhibitors, growth factor inhibitors, heat shock protein (HSP)-90 inhibitors, histone deacetylase (HDAC) inhibitors, hormonal therapies, immunologicals, inhibitors of inhibitors of apoptosis proteins (IAPs), intercalating antibiotics, kinase inhibitors, kinesin inhibitors, Jak2 inhibitors, mammalian target of rapamycin inhibitors, microRNA's, mitogen-activated extracellular signal-regulated kinase inhibitors, multivalent binding proteins, non-steroidal anti-inflammatory drugs (NSAIDs), poly ADP (adenosine diphosphate)-ribose polymerase (PARP) inhibitors, platinum chemotherapeutics, polo-like kinase (Plk) inhibitors, phosphoinositide-3 kinase (PI3K) inhibitors, proteosome inhibitors, purine analogs, pyrimidine analogs, receptor tyrosine kinase inhibitors, etinoids/deltoids plant alkaloids, small inhibitory ribonucleic acids (siRNAs), topoisomerase inhibitors, ubiquitin ligase inhibitors, and the like, and in combination with one or more of these agents.

BiTE antibodies are bi-specific antibodies that direct T-cells to attack cancer cells by simultaneously binding the two cells. The T-cell then attacks the target cancer cell. Examples of BiTE antibodies include adecatumumab (Micromet MT201), blinatumomab (Micromet MT103) and the like. Without being limited by theory, one of the mechanisms by which T-cells elicit apoptosis of the target cancer cell is by exocytosis of cytolytic granule components, which include perforin and granzyme B. In this regard, Bcl-2 has been shown to attenuate the induction of apoptosis by both perforin and granzyme B. These data suggest that inhibition of Bcl-2 could enhance the cytotoxic effects elicited by T-cells when targeted to cancer cells (V. R. Sutton, D. L. Vaux and J. A. Trapani, *J. of Immunology* 1997, 158 (12), 5783).

SiRNAs are molecules having endogenous RNA bases or chemically modified nucleotides. The modifications do not abolish cellular activity, but rather impart increased stability and/or increased cellular potency. Examples of chemical modifications include phosphorothioate groups, 2'-deoxynucleotide, 2'-OCH$_3$-containing ribonucleotides, 2'-F-ribonucleotides, 2'-methoxyethyl ribonucleotides, combinations thereof and the like. The siRNA can have varying lengths (e.g., 10-200 bps) and structures (e.g., hairpins, single/double strands, bulges, nicks/gaps, mismatches) and are processed in cells to provide active gene silencing. A double-stranded siRNA (dsRNA) can have the same number of nucleotides on each strand (blunt ends) or asymmetric ends (overhangs). The overhang of 1-2 nucleotides can be present on the sense and/or the antisense strand, as well as present on the 5'-and/or the 3'-ends of a given strand.

Multivalent binding proteins are binding proteins comprising two or more antigen binding sites. Multivalent binding proteins are engineered to have the three or more antigen binding sites and are generally not naturally occurring antibodies. The term "multispecific binding protein" means a binding protein capable of binding two or more related or unrelated targets. Dual variable domain (DVD) binding proteins are tetravalent or multivalent binding proteins binding proteins comprising two or more antigen binding sites. Such DVDs may be monospecific (i.e., capable of binding one antigen) or multispecific (i.e., capable of binding two or more antigens). DVD binding proteins comprising two heavy chain DVD polypeptides and two light chain DVD polypeptides are referred to as DVD Ig's. Each half of a DVD Ig comprises a heavy chain DVD polypeptide, a light chain DVD polypeptide, and two antigen binding sites. Each binding site comprises a heavy chain variable domain and a light chain variable domain with a total of 6 CDRs involved in antigen binding per antigen binding site. Multispecific DVDs include DVD binding proteins that bind DLL4 and VEGF, or C-met and EFGR or ErbB3 and EGFR.

Alkylating agents include altretamine, AMD-473, AP-5280, apaziquone, bendamustine, brostallicin, busulfan, carboquone, carmustine (BCNU), chlorambucil, CLORETAZINE® (laromustine, VNP 40101M), cyclophosphamide, decarbazine, estramustine, fotemustine, glufosfamide, ifosfamide, KW-2170, lomustine (CCNU), mafosfamide, melphalan, mitobronitol, mitolactol, nimustine, nitrogen mustard N-oxide, ranimustine, temozolomide, thiotepa, TREANDA® (bendamustine), treosulfan, rofosfamide and the like.

Angiogenesis inhibitors include endothelial-specific receptor tyrosine kinase (Tie-2) inhibitors, epidermal growth factor receptor (EGFR) inhibitors, insulin growth factor-2 receptor (IGFR-2) inhibitors, matrix metalloproteinase-2 (MMP-2) inhibitors, matrix metalloproteinase-9 (MMP-9) inhibitors, platelet-derived growth factor receptor (PDGFR) inhibitors, thrombospondin analogs, vascular endothelial growth factor receptor tyrosine kinase (VEGFR) inhibitors and the like.

Antimetabolites include ALIMTA® (pemetrexed disodium, LY231514, MTA), 5-azacitidine, XELODA® (capecitabine), carmofur, LEUSTAT® (cladribine), clofarabine, cytarabine, cytarabine ocfosfate, cytosine arabinoside, decitabine, deferoxamine, doxifluridine, eflornithine, EICAR (5-ethynyl-1-β-D-ribofuranosylimidazole-4-carboxamide), enocitabine, ethnylcytidine, fludarabine, 5-fluorouracil alone or in combination with leucovorin, GEMZAR® (gemcitabine), hydroxyurea, ALKERAN®(melphalan), mercaptopurine, 6-mercaptopurine riboside, methotrexate, mycophenolic acid, nelarabine, nolatrexed, ocfosfate, pelitrexol, pentostatin, raltitrexed, Ribavirin, triapine, trimetrexate, S-1, tiazofurin, tegafur, TS-1, vidarabine, UFT and the like.

Antivirals include ritonavir, hydroxychloroquine and the like.

Aurora kinase inhibitors include ABT-348, AZD-1152, MLN-8054, VX-680, Aurora A-specific kinase inhibitors, Aurora B-specific kinase inhibitors and pan-Aurora kinase inhibitors and the like.

Bcl-2 protein inhibitors include AT-101 ((−)gossypol), GENASENSE® (G3139 or oblimersen (Bcl-2-targeting antisense oligonucleotide)), IPI-194, IPI-565, N-(4-(4-((4'-chloro(1,1'-biphenyl)-2-yl)methyl)piperazin-1-yl)benzoyl)-4-(((1R)-3-(dimethylamino)-1-((phenylsulfanyl)methyl) propyl)amino)-3-nitrobenzenesulfonamide) (ABT-737), N-(4-(4-((2-(4-chlorophenyl)-5,5-dimethyl-1-cyclohex-1-en-1-yl)methyl)piperazin-1-yl)benzoyl)-4-(((1R)-3-(morpholin-4-yl)-1-((phenylsulfanyl)methyl)propyl)amino)-3-((trifluoromethyl)sulfonyl)benzenesulfonamide (ABT-263), GX-070 (obatoclax) and the like.

Bcr-Abl kinase inhibitors include DASATINIB® (BMS-354825), GLEEVEC® (imatinib) and the like.

CDK inhibitors include AZD-5438, BMI-1040, BMS-032, BMS-387, CVT-2584, flavopyridol, GPC-286199, MCS-5A, PD0332991, PHA-690509, seliciclib (CYC-202, R-roscovitine), ZK-304709 and the like.

COX-2 inhibitors include ABT-963, ARCOXIA® (etoricoxib), BEXTRA® (valdecoxib), BMS347070, CELEBREX® (celecoxib), COX-189 (lumiracoxib), CT-3, DERAMAXX® (deracoxib), JTE-522, 4-methyl-2-(3,4-dimethylphenyl)-1-(4-sulfamoylphenyl-1H-pyrrole), MK-663 (etoricoxib), NS-398, parecoxib, RS-57067, SC-58125, SD-8381, SVT-2016, S-2474, T-614, VIOXX® (rofecoxib) and the like.

EGFR inhibitors include ABX-EGF, anti-EGFR immunoliposomes, EGF-vaccine, EMD-7200, ERBITUX® (cetuximab), HR3, IgA antibodies, IRESSA® (gefitinib), TARCEVA® (erlotinib or OSI-774), TP-38, EGFR fusion protein, TYKERB® (lapatinib) and the like.

ErbB2 receptor inhibitors include CP-724-714, CI-1033 (canertinib), HERCEPTIN® (trastuzumab), TYKERB® (lapatinib), OMNITARG® (2C4, petuzumab), TAK-165, GW-572016 (ionafarnib), GW-282974, EKB-569, PI-166, dHER2 (HER2 vaccine), APC-8024 (HER-2 vaccine), anti-HER/2neu bispecific antibody, B7.her2IgG3, AS HER2 trifunctional bispecfic antibodies, mAB AR-209, mAB 2B-1 and the like.

Histone deacetylase inhibitors include depsipeptide, LAQ-824, MS-275, trapoxin, suberoylanilide hydroxamic acid (SAHA), TSA, valproic acid and the like.

HSP-90 inhibitors include 17-AAG-nab, 17-AAG, CNF-101, CNF-1010, CNF-2024, 17-DMAG, geldanamycin, IPI-504, KOS-953, MYCOGRAB® (human recombinant antibody to HSP-90), NCS-683664, PU24FC1, PU-3, radicicol, SNX-2112, STA-9090 VER49009 and the like.

Inhibitors of inhibitors of apoptosis proteins include HGS 1029, GDC-0145, GDC-0152, LCL-161, LBW-242 and the like.

Antibody drug conjugates include anti-CD22-MC-MMAF, anti-CD22-MC-MMAE, anti-CD22-MCC-DM1, CR-011-vcMMAE, PSMA-ADC, MEDI-547, SGN-19Am SGN-35, SGN-75 and the like Activators of death receptor pathway include TRAIL, antibodies or other agents that target TRAIL or death receptors (e.g., DR4 and DR5) such as Apomab, conatumumab, ETR2-ST01, GDC0145, (lexatumumab), HGS-1029, LBY-135, PRO-1762 and trastuzumab.

Kinesin inhibitors include Eg5 inhibitors such as AZD4877, ARRY-520; CENPE inhibitors such as GSK923295A and the like.

JAK-2 inhibitors include CEP-701 (lesaurtinib), XL019 and INCB018424 and the like.

MEK inhibitors include ARRY-142886, ARRY-438162 PD-325901, PD-98059 and the like.

mTOR inhibitors include AP-23573, CCI-779, everolimus, RAD-001, rapamycin, temsirolimus, ATP-competitive TORC1/TORC2 inhibitors, including PI-103, PP242, PP30, Torin 1 and the like.

Non-steroidal anti-inflammatory drugs include AMIGESIC® (salsalate), DOLOBID® (diflunisal), MOTRIN® (ibuprofen), ORUDIS® (ketoprofen), RELAFEN® (nabumetone), FELDENE® (piroxicam), ibuprofen cream, ALEVE® (naproxen) and NAPROSYN® (naproxen), VOLTAREN® (diclofenac), INDOCIN® (indomethacin), CLINORIL® (sulindac), TOLECTIN® (tolmetin), LODINE® (etodolac), TORADOL® (ketorolac), DAYPRO® (oxaprozin) and the like.

PDGFR inhibitors include C-451, CP-673, CP-868596 and the like.

Platinum chemotherapeutics include cisplatin, ELOXATIN® (oxaliplatin) eptaplatin, lobaplatin, nedaplatin, PARAPLATIN® (carboplatin), satraplatin, picoplatin and the like.

Polo-like kinase inhibitors include BI-2536 and the like.

Phosphoinositide-3 kinase (PI3K) inhibitors include wortmannin, LY294002, XL-147, CAL-120, ONC-21, AEZS-127, ETP-45658, PX-866, GDC-0941, BGT226, BEZ235, XL765 and the like.

Thrombospondin analogs include ABT-510, ABT-567, ABT-898, TSP-1 and the like.

VEGFR inhibitors include AVASTIN® (bevacizumab), ABT-869, AEE-788, ANGIOZYME™ (a ribozyme that inhibits angiogenesis (Ribozyme Pharmaceuticals (Boulder, Colo.) and Chiron, (Emeryville, Calif.)), axitinib (AG-13736), AZD-2171, CP-547,632, IM-862, MACUGEN (pegaptamib), NEXAVAR® (sorafenib, BAY43-9006), pazopanib (GW-786034), vatalanib (PTK-787, ZK-222584), SUTENT® (sunitinib, SU-11248), VEGF trap, ZACTIMA™ (vandetanib, ZD-6474), GA101, ofatumumab, ABT-806 (mAb-806), ErbB3 specific antibodies, BSG2 specific antibodies, DLL4 specific antibodies and C-met specific antibodies, and the like.

Antibiotics include intercalating antibiotics aclarubicin, actinomycin D, amrubicin, annamycin, adriamycin, BLENOXANE® (bleomycin), daunorubicin, CAELYX® or MYOCET® (liposomal doxorubicin), elsamitrucin, epirubicin, glarbuicin, ZAVEDOS® (idarubicin), mitomycin C, nemorubicin, neocarzinostatin, peplomycin, pirarubicin, rebeccamycin, stimalamer, streptozocin, VALSTAR® (valrubicin), zinostatin and the like.

Topoisomerase inhibitors include aclarubicin, 9-aminocamptothecin, amonafide, amsacrine, becatecarin, belotecan, BN-80915, CAMPTOSAR® (irinotecan hydrochloride), camptothecin, CARDIOXANE® (dexrazoxine), diflomotecan, edotecarin, ELLENCE® or PHARMORUBICIN® (epirubicin), etoposide, exatecan, 10-hydroxycamptothecin, gimatecan, lurtotecan, mitoxantrone, orathecin, pirarbucin, pixantrone, rubitecan, sobuzoxane, SN-38, tafluposide, topotecan and the like.

Antibodies include AVASTIN® (bevacizumab), CD40-specific antibodies, chTNT-1/B, denosumab, ERBITUX® (cetuximab), HUMAX-CD4® (zanolimumab), IGF1R-specific antibodies, lintuzumab, PANOREX® (edrecolomab), RENCAREX® (WX G250), RITUXAN® (rituximab), ticilimumab, trastuzimab, CD20 antibodies types I and II and the like.

Hormonal therapies include ARIMIDEX® (anastrozole), AROMASIN® (exemestane), arzoxifene, CASODEX® (bicalutamide), CETROTIDE® (cetrorelix), degarelix, deslorelin, DESOPAN® (trilostane), dexamethasone, DROGENIL® (flutamide), EVISTA® (raloxifene), AFEMA™ (fadrozole), FARESTON® (toremifene), FASLODEX® (fulvestrant), FEMARA® (letrozole), formestane, glucocorticoids, HECTOROL® (doxercalciferol), RENAGEL® (sevelamer carbonate), lasofoxifene, leuprolide acetate, MEGACE® (megesterol), MIFEPREX® (mifepristone), NILANDRON™ (nilutamide), NOLVADEX® (tamoxifen citrate), PLENAXIS™ (abarelix), prednisone, PROPECIA® (finasteride), rilostane, SUPREFACT® (buserelin), TRELSTAR® (luteinizing hormone releasing hormone (LHRH)), VANTAS® (Histrelin implant), VETORYL® (trilostane or modrastane), ZOLADEX® (fosrelin, goserelin) and the like.

Deltoids and retinoids include seocalcitol (EB1089, CB1093), lexacalcitrol (KH1060), fenretinide, PANRETIN® (aliretinoin), ATRAGEN® (liposomal tretinoin), TARGRETIN® (bexarotene), LGD-1550 and the like.

PARP inhibitors include ABT-888 (veliparib), olaparib, KU-59436, AZD-2281, AG-014699, BSI-201, BGP-15, INO-1001, ONO-2231 and the like.

Plant alkaloids include, but are not limited to, vincristine, vinblastine, vindesine, vinorelbine and the like.

Proteasome inhibitors include VELCADE® (bortezomib), MG132, NPI-0052, PR-171 and the like.

Examples of immunologicals include interferons and other immune-enhancing agents. Interferons include interferon alpha, interferon alpha-2a, interferon alpha-2b, interferon beta, interferon gamma-1a, ACTIMMUNE® (interferon gamma-1b) or interferon gamma-n1, combinations thereof and the like. Other agents include ALFAFERONE°, (IFN-α), BAM-002 (oxidized glutathione), BEROMUN® (tasonermin), BEXXAR® (tositumomab), CAMPATH® (alemtuzumab), CTLA4 (cytotoxic lymphocyte antigen 4), decarbazine, denileukin, epratuzumab, GRANOCYTE® (lenograstim), lentinan, leukocyte alpha interferon, imiquimod, MDX-010 (anti-CTLA-4), melanoma vaccine, mitumomab, molgramostim, MYLOTARG™ (gemtuzumab ozogamicin), NEUPOGEN® (filgrastim), OncoVAC-CL, OVAREX® (oregovomab), pemtumomab (Y-muHMFG1), PROVENGE® (sipuleucel-T), sargaramostim, sizofilan, teceleukin, THERACYS® (Bacillus Calmette-Guerin), ubenimex, VIRULIZIN° (immunotherapeutic, Lorus Pharmaceuticals), Z-100 (Specific Substance of Maruyama (SSM)), WF-10 (Tetrachlorodecaoxide (TCDO)), PROLEUKIN® (aldesleukin), ZADAXIN® (thymalfasin), ZENAPAX® (daclizumab), ZEVALIN® (90Y-Ibritumomab tiuxetan) and the like.

Biological response modifiers are agents that modify defense mechanisms of living organisms or biological responses, such as survival, growth or differentiation of tissue cells to direct them to have anti-tumor activity and include krestin, lentinan, sizofiran, picibanil PF-3512676 (CpG-8954), ubenimex and the like.

Pyrimidine analogs include cytarabine (ara C or Arabinoside C), cytosine arabinoside, doxifluridine, FLUDARA® (fludarabine), 5-FU (5-fluorouracil), floxuridine, GEMZAR® (gemcitabine), TOMUDEX® (ratitrexed), TROXATYL™ (triacetyluridine troxacitabine) and the like.

Purine analogs include LANVIS® (thioguanine) and PURI-NETHOL® (mercaptopurine).

Antimitotic agents include batabulin, epothilone D (KOS-862), N-(2-((4-hydroxyphenyl)amino)pyridin-3-yl)-4-methoxybenzenesulfonamide, ixabepilone (BMS 247550), paclitaxel, TAXOTERE® (docetaxel), PNU100940 (109881), patupilone, XRP-9881 (larotaxel), vinflunine, ZK-EPO (synthetic epothilone) and the like.

Ubiquitin ligase inhibitors include MDM2 inhibitors, such as nutlins, NEDD8 inhibitors such as MLN4924 and the like.

Compounds of this invention can also be used as radiosensitizers that enhance the efficacy of radiotherapy. Examples of radiotherapy include external beam radiotherapy, teletherapy, brachytherapy and sealed, unsealed source radiotherapy and the like.

Additionally, compounds having Formula (I) may be combined with other chemotherapeutic agents such as ABRAXANE™ (ABI-007), ABT-100 (farnesyl transferase inhibitor), ADVEXIN® (Ad5CMV-p53 vaccine), ALTOCOR® or MEVACOR® (lovastatin), AMPLIGEN® (poly I:poly C12U, a synthetic RNA), APTOSYN® (exisulind), AREDIA® (pamidronic acid), arglabin, L-asparaginase, atamestane (1-methyl-3,17-dione-androsta-1,4-diene), AVAGE® (tazarotene), AVE-8062 (combreastatin derivative) BEC2 (mitumomab), cachectin or cachexin (tumor necrosis factor), canvaxin (vaccine), CEAVAC® (cancer vaccine), CELEUK® (celmoleukin), CEPLENE® (histamine dihydrochloride), CERVARIX® (human papillomavirus vaccine), CHOP® (C: CYTOXAN® (cyclophosphamide); H: ADRIAMYCIN® (hydroxydoxorubicin); O: Vincristine (ONCOVIN®); P: prednisone), CYPAT™ (cyproterone acetate), combrestatin A4P, DAB(389)EGF (catalytic and translocation domains of diphtheria toxin fused via a His-Ala linker to human epidermal growth factor) or TransMID-107R™ (diphtheria toxins), dacarbazine, dactinomycin, 5,6-dimethylxanthenone-4-acetic acid (DMXAA), eniluracil, EVIZON™ (squalamine lactate), DIMERICINE® (T4N5 liposome lotion), discodermolide, DX-8951f (exatecan mesylate), enzastaurin, EP0906 (epithilone B), GARDASIL® (quadrivalent human papillomavirus (Types 6, 11, 16, 18) recombinant vaccine), GASTRIMMUNE®, GENASENSE®, GMK (ganglioside conjugate vaccine), GVAX® (prostate cancer vaccine), halofuginone, histerelin, hydroxycarbamide, ibandronic acid, IGN-101, IL-13-PE38, IL-13-PE38QQR (cintredekin besudotox), IL-13-pseudomonas exotoxin, interferon-α, interferon-γ, JUNOVAN™ or MEPACT™ (mifamurtide), lonafarnib, 5,10-methylenetetrahydrofolate, miltefosine (hexadecylphosphocholine), NEOVASTAT® (AE-941), NEUTREXIN® (trimetrexate glucuronate), NIPENT® (pentostatin), ONCONASE® (a ribonuclease enzyme), ONCOPHAGE® (melanoma vaccine treatment), ONCOVAX® (IL-2 Vaccine), ORATHECIN™ (rubitecan), OSIDEM® (antibody-based cell drug), OVAREX® MAb (murine monoclonal antibody), paclitaxel, PANDIMEX™ (aglycone saponins from ginseng comprising 20(S)protopanaxadiol (aPPD) and 20(S)protopanaxatriol (aPPT)), panitumumab, PANVAC®-VF (investigational cancer vaccine), pegaspargase, PEG Interferon A, phenoxodiol, procarbazine, rebimastat, REMOVAB® (catumaxomab), REVLIMID® (lenalidomide), RSR13 (efaproxiral), SOMATULINE® LA (lanreotide), SORIATANE® (acitretin), staurosporine (*Streptomyces* staurospores), talabostat (PT100), TARGRETIN® (bexarotene), TAXOPREXIN® (DHA-paclitaxel), TELCYTA® (canfosfamide, TLK286), temilifene, TEMODAR® (temozolomide), tesmilifene, thalidomide, THERATOPE® (STn-KLH), thymitaq (2-amino-3,4-dihydro-6-methyl-4-oxo-5-(4-pyridylthio)quinazoline dihydrochloride), TNFERADE™ (adenovector: DNA carrier containing the gene for tumor necrosis factor-α), TRACLEER® or ZAVESCA® (bosentan), tretinoin (Retin-A), tetrandrine, TRISENOX® (arsenic trioxide), VIRULIZIN®, ukrain (derivative of alkaloids from the greater celandine plant), vitaxin (anti-alphavbeta3 antibody), XCYTRIN® (motexafin gadolinium), XINLAY™ (atrasentan), XYOTAX™ (paclitaxel poliglumex), YONDELIS® (trabectedin), ZD-6126, ZINECARD® (dexrazoxane), ZOMETA® (zolendronic acid), zorubicin and the like.

EXAMPLES

Example 1

4-benzyl-6-(1H-pyrrolo[2,3-b]pyridin-3-yl)phthalazin-1(2H)-one

Example 1A 3,5-Dibromo-3H-isobenzofuran-1-one

To a suspension of 5-bromoisobenzofuran-1(3H)-one (5 g, 23.5 mmol) in anhydrous carbon tetrachloride (50 mL) was added N-bromosuccinimide (4.18 g, 23.5 mmol) and a catalytic amount of benzoyl peroxide. The reaction mixture was heated under reflux for 2.5 hours. After cooling, the precipitated solid was filtered off, and the filtrate was concentrated on a rotary evaporator. The residual solid was partitioned between methylene chloride and water. The organic phase was washed with brine, and concentrated. The residue was purified by flash chromatography on silica gel eluting with 20% ethyl acetate in hexanes to yield the title compound. MS (ESI) m/z 290 (M+H)$^+$.

Example 1B

5-Bromo-3-hydroxy-3H-isobenzofuran-1-one

To a suspension of EXAMPLE 1A (5 g, 17.1 mmol) in water (40 mL) was added powdered potassium hydroxide (1.92 g, 34.3 mmol), and the mixture was refluxed for 1 hour. After cooling, potassium bisulfate (2 g) was added, and the mixture extracted with ethyl acetate (150 mL). The organics were concentrated on a rotary evaporator and dried under vacuum to yield the title compound. MS (ESI) m/z 230 (M+H)$^+$.

Example 1C (6-Bromo-3-oxo-1,3-dihydro-isobenzofuran-1-yl)-phosphonic acid dimethyl ester To a 0.5 M solution of sodium methoxide in methanol (39.6 mL, 19.8 mmol) was added dimethyl phosphite (2.6 mL, 28.6 mmol) at 0° C., and the solution was stirred at at 0° C. for 10 minutes. A suspension of the EXAMPLE 1B (3.24 g, 14.15 mmol) in anhydrous methanol (20 mL) was slowly added and the reaction mixture allowed to warm to room temperature over a period of 1 hour. The solution was cooled in an ice-bath, and methanesulfonic acid (2.0 mL, 31.1 mmol) was added dropwise. After the addition, the mixture was concentrated on a rotary evaporator. The concentrate was partitioned between methylene chloride (100 mL) and water (50 mL). The organics was washed with brine (50 mL), and concentrated. The residue was dried under vacuum to yield the title compound. MS (ESI) m/z 322 (M+H)+.

Example 1D

3-Benzylidene-5-bromo-3H-isobenzofuran-1-one

To a solution of EXAMPLE 1C (4.6 g, 14.08 mmol) in anhydrous tetrahydrofuran (30 mL) was added benzaldehyde (0.71 mL, 7.4 mmol) and triethylamine (1.00 mL, 7.39 mmol). The reaction mixture was stirred at ambient temperature overnight. Water was added and the mixture stirred for 10 minutes. The precipitated solid was filtered and dried under vacuum to yield the title compound. MS (ESI) m/z 302 (M+H)+.

Example 1E

4-Benzyl-6-bromo-2H-phthalazin-1-one

To a solution of EXAMPLE 1D (778 mg, 2.58 mmol) in ethanol (10 mL) was added hydrazine (83 mg, 2.58 mmol) and the mixture was refluxed for 2 hours. After cooling, the precipitated solid was collected by filtration and dried under vacuum to yield the title compound. MS (ESI) m/z 316 (M+H)+.

Example 1F

3-Bromo-1H-pyrrolo[2,3-b]pyridine

To a solution of 1H-pyrrolo[2,3-b]pyridine (15.6 g, 132 mmol) in 400 mL tetrahydrofuran at −40° C. was added a suspension of N-bromosuccinimide in 120 mL tetrahydrofuran. The reaction mixture was warmed to room temperature and allowed to stir for 4 hours. The solid was filtered off. The reaction mixture was quenched with a sodium metabisulfite solution, and extracted with ethyl acetate. The combined organics were washed with brine, dried over MgSO$_4$, filtered, and concentrated. The residue was triturated with 1:1 hexane/ethyl acetate and filtered. The filtrate was concentrated and the trituration step was repeated three more times to afford the title compound, which was used without further purification. MS (DCI−) m/z 196.9 (M+H)+.

Example 1G

3-Bromo-1-(phenylsulfonyl)-1H-pynolo[2,3-b]pyridine

To a 0° C. solution of EXAMPLE 1F (25 g, 127 mmol) in N,N-dimethylformamide (200 mL) was slowly added sodium hydride (3.37 g, 133 mmol) over several minutes. After stirring for 30 minutes in the cold water bath, benzenesulfonyl chloride (17.18 ml, 133 mmol) was added via a syringe. The solution was allowed to warm to room temperature overnight, quenched slowly with 500 mL water, stirred for 30 minutes, and then filtered. The solid obtained was washed with water, followed by 300 mL of hexanes, dried over high-vacuum for 16 hours to give the title compound which was used without further purification. MS (ESL) m/z 338.7 (M+H)+.

Example 1H 1-(Phenylsulfonyl)-3-(4,4,5,5-tetramethyl-1,3,2-dioxaborolan-2-yl)-1H-pynolo[2,3-b]pyridine A mixture of EXAMPLE 1G (2.5 g, 7 mmol), dichlorobis (triphenylphosphine)palladium(II) (0.24 g, 0.29 mmol), bis (pinacolato)diboron (2.07 g, 8.15 mmol), and potassium acetate (2.18 g, 22 mmol) in degassed tetrahydrofuran (5 mL) was sealed and heated in a microwave (Biotage Initiator 8 or CEM Explorer at 200 W) at 140° C. for 20 minutes. The reaction mixture was cooled to room temperature, diluted with ethyl acetate, and washed with water. The aqueous layer was separated and extracted with dichloromethane. The combined organics were washed with brine, dried over MgSO$_4$, filtered, and concentrated. The residue was purified on silica gel using flash chromatography (20% ethyl acetate/hexane) to afford the title compound. MS (ESL) m/z 385.0 (M+H)+.

Example 1I 4-benzyl-6-(1H-pyrrolo[2,3-b]pyridin-3-yl)phthalazin-1(2H)-one

A suspension of EXAMPLE 1E (75 mg, 0.24 mmol), Example 1H (91 mg, 0.24 mmol), [1,1'-bis(diphenylphosphino)-ferrocene]dichloropalladium(II) adduct with dichloromethane (19.4 mg, 0.024 mmol) and potassium carbonate (66 mg, 0.48 mmol) in a 7:3:2 mixture of dimethoxyethane:water:ethanol (3 mL) was heated in a Biotage Initiator microwave at 150° C. for 20 minutes. After cooling, the reaction mixture was partitioned between ethyl acetate and brine. The organic phase was washed with water and concentrated. The residue was purified by flash chromatography on silica gel eluting with 5% methanol in dichloromethane. The obtained product was dissolved in ethanol (5 mL), and treated with sodium hydroxide (19 mg, 0.48 mmol) at 90° C. for 1 hour. The reaction mixture was cooled and concentrated on a rotary evaporator. The residue was dissolved in a dimethylsulfoxide/methanol mixture, and purified by HPLC (Zorbax C-18, 0-100% gradient acetonitrile in water containing 0.1% trifluoroacetic acid) to yield the title compound. MS (ESI) m/z 353 (M+H)+. $^1$H NMR (300 MHz, DMSO-d$_6$) δ 4.41 (s, 2H), 7.14 (dd, J=7.97, 4.58 Hz, 1H), 7.22-7.30 (m, 1H), 7.34-7.38 (m, 4H), 7.78 (dd, J=8.14, 1.02 Hz, 1H), 8.01 (d, J=1.36 Hz, 1H), 8.11 (d, J=2.71 Hz, 1H), 8.14 (dd, J=8.48, 1.70 Hz, 1H), 8.26 (d, J=8.14 Hz, 1H), 8.30 (dd, J=4.75, 1.36 Hz, 1H), 12.16 (br s, 1H), 12.52 (br s, 1H).

Example 2

4-benzyl-6-(pyridin-4-yl)phthalazin-1(2H)-one

A suspension of EXAMPLE 1E (75 mg, 0.24 mmol), pyridin-4-ylboronic acid (44 mg, 0.36 mmol), [1,1'-bis(diphenylphosphino)-ferrocene]dichloropalladium(II)aaduct with dichloromethane (19.4 mg, 0.024 mmol) and potassium carbonate (66 mg, 0.48 mmol) in a mixture of 7:3:2 dimethoxyethane:water:ethanol (3 mL) was heated in a Biotage Initiator microwave at 150° C. for 20 minutes. The volatiles were removed, and the residue was purified by HPLC (Zorbax C-18, 0-100% gradient acetonitrile in water containing 0.1% trifluoroacetic acid) to yield the title compound. MS (ESI) m/z 314 (M+H)+. $^1$H NMR (300 MHz, DMSO-d$_6$) δ 4.44 (s, 2H), 7.20 (d, J=7.14 Hz, 1H), 7.27-7.33 (m, 2H), 7.34-7.40 (m, 2H), 7.95 (d, J=6.35 Hz, 2H), 8.22-8.28 (m, 1H), 8.32-8.41 (m, 2H), 8.78-8.84 (m, 2H), 12.68 (br s, 1H).

Example 3

4-benzyl-6-(1H-pyrazol-4-yl)phthalazin-1(2H)-one

The title compound was prepared as described in EXAMPLE 2, substituting tert-butyl 4-(4,4,5,5-tetramethyl-1,3,2-dioxaborolan-2-yl)-1H-pyrazole-1-carboxylate for pyridin-4-ylboronic acid. MS (ESI) m/z 303 (M+H)+. $^1$H NMR (300 MHz, DMSO-$d_6$) δ 4.35 (s, 2H), 7.14-7.23 (m, 1H), 7.25-7.33 (m, 2H), 7.37-7.45 (m, 2H), 8.01-8.12 (m, 3H), 8.19 (d, J=8.14 Hz, 1H), 8.35-8.43 (m, 1H), 12.45 (br s, 1H), 13.17 (br s, 1H).

Example 4

4-benzyl-6-(pyridin-3-yl)phthalazin-1(2H)-one

The title compound was prepared as described in EXAMPLE 2, substituting pyridin-3-ylboronic acid for pyridin-4-ylboronic acid. MS (ESI) m/z 314 (M+H)+; $^1$H NMR (300 MHz, DMSO-$d_6$) δ 4.43 (s, 2H), 7.15-7.22 (m, 1H), 7.26-7.33 (m, 2H), 7.34-7.40 (m, 2H), 7.64 (dd, J=7.93, 4.76 Hz, 1H), 8.15-8.21 (m, 1H), 8.23-8.30 (m, 2H), 8.35 (d, J=8.33 Hz, 1H), 8.70 (dd, J=4.96, 1.39 Hz, 1H), 9.00 (d, J=1.59 Hz, 1H), 12.64 (br s, 1H).

Example 5

4-(pyridin-4-ylmethyl)-6-(1H-pyrrolo[2,3-b]pyridin-3-yl)phthalazin-1(2H)-one

Example 5A

5-Bromo-3-pyridin-4-ylmethylene-3H-isobenzofuran-1-one

The title compound was prepared as described in EXAMPLE 1D, substituting isonicotinaldehyde for benzaldehyde. MS (ESI) m/z 303 (M+H)+.

Example 5B

6-Bromo-4-pyridin-4-ylmethyl-2H-phthalazin-1-one

The title compound was prepared as described in EXAMPLE 1E, substituting EXAMPLE 5A for EXAMPLE 1D. MS (ESI) m/z 317 (M+H)+.

Example 5C 4-(pyridin-4-ylmethyl)-6-(1H-pyrrolo[2,3-b]pyridin-3-yl)phthalazin-1(2H)-one The title compound was prepared as described in EXAMPLE 1I, substituting EXAMPLE 5B for EXAMPLE 1E. MS (ESI) m/z 354 (M+H)+. $^1$H NMR (300 MHz, DMSO-$d_6$) δ 4.59 (s, 2H), 7.20 (dd, J=8.14, 4.75 Hz, 1H), 7.78 (d, J=6.10 Hz, 2H), 8.07 (d, J=1.02 Hz, 1H), 8.09-8.15 (m, 1H), 8.20 (d, J=2.71 Hz, 1H), 8.21-8.25 (m, 1H), 8.30 (d, J=8.81 Hz, 1H), 8.32-8.34 (m, 1H), 8.73 (d, J=6.10 Hz, 2H), 12.23 (br s, 1H), 12.56 (br s, 1H).

Example 6

4-(2,5-dichlorobenzyl)-6-(1H-pyrrolo[2,3-b]pyridin-3-yl)phthalazin-1(2H)-one

The title compound was prepared as described in EXAMPLE 5, substituting 2,4-dichlorobenzaldehyde for isonicotinaldehyde. MS (ESI) m/z 422 (M+H)+; $^1$H NMR (300 MHz, DMSO-$d_6$) δ 4.53 (s, 2H), 7.20 (dd, J=8.14, 4.75 Hz, 1H), 7.35-7.42 (m, 2H), 7.70 (d, J=1.70 Hz, 1H), 8.09 (d, J=1.36 Hz, 1H), 8.16 (dd, J=8.14, 1.36 Hz, 1H), 8.22 (d, J=2.37 Hz, 1H), 8.24 (d, J=1.36 Hz, 1H), 8.28-8.31 (m, 1H), 8.33 (dd, J=4.75, 1.36 Hz, 1H), 12.22 (br s, 1H), 12.43 (br s, 1H).

Example 7

4-(piperidin-3-ylmethyl)-6-(1H-pyrrolo[2,3-b]pyridin-3-yl)phthalazin-1(2H)-one

The title compound was prepared as described in EXAMPLE 9, substituting tert-butyl 3-formylpiperidine-1-carboxylate for tert-butyl 4-formylpiperidine-1-carboxylate. MS (ESI) m/z 360 (M+H)+; $^1$H NMR (300 MHz, DMSO-$d_6$) δ 1.23-1.43 (m, 1H), 1.51-1.68 (m, 1H), 1.74-1.93 (m, 2H), 2.22-2.35 (m, 1H), 2.69-2.85 (m, 2H), 2.96-3.06 (m, 2H), 3.19-3.34 (m, 2H), 7.25 (dd, J=8.14, 4.75 Hz, 1H), 8.13-8.17 (m, 1H), 8.22-8.25 (m, 1H), 8.25-8.27 (m, 1H), 8.29-8.33 (m, 1H), 8.35 (dd, J=4.58, 1.53 Hz, 1H), 8.41-8.44 (m, 1H), 8.49 (br s, 1H), 12.27 (br s, 1H), 12.49 (br s, 1H).

Example 8

4-(pyridin-3-ylmethyl)-6-(1H-pyrrolo[2,3-b]pyridin-3-yl)phthalazin-1(2H)-one

The title compound was prepared as described in EXAMPLE 5, substituting nicotinaldehyde for isonicotinaldehyde. MS (ESI) m/z 354 (M+H)+; $^1$H NMR (300 MHz, DMSO-$d_6$) δ 4.59 (s, 2H), 7.21 (dd, J=7.97, 4.58 Hz, 1H), 7.67 (dd, J=7.63, 5.26 Hz, 1H), 8.10 (d, J=8.14 Hz, 1H), 8.14-8.19 (m, 2H), 8.21 (d, J=2.71 Hz, 1H), 8.22-8.25 (m, 1H), 8.28-8.31 (m, 1H), 8.33 (dd, J=4.58, 1.53 Hz, 1H), 8.63 (dd, J=5.09, 1.36 Hz, 1H), 8.80 (d, J=1.70 Hz, 1H), 12.23 (br s, 1H), 12.49 (br s, 1H).

Example 9

4-(piperidin-4-ylmethyl)-6-(1H-pyrrolo[2,3-b]pyridin-3-yl)phthalazin-1(2H)-one

Example 9A 4-(6-Bromo-3-oxo-3H-isobenzofuran-1-ylidenemethyl)-piperidine-1-carboxylic acid tert-butyl ester The title compound was prepared as described in EXAMPLE 1D, substituting tert-butyl 4-formylpiperidine-1-carboxylate for benzaldehyde. MS (ESI) m/z 410 (M+H)+.

Example 9B

4-[7-(1-Benzenesulfonyl-1H-pyrrolo[2,3-b]pyridin-3-yl)-4-oxo-3,4-dihydro-phthalazin-1-ylmethyl]-piperidine-1-carboxylic acid tert-butyl ester A mixture of EXAMPLE 9A (527 mg, 1.3 mmol), Example 1H (546 mg, 1.42 mmol), [1,1'-bis(diphenylphosphino)-ferrocene]-dichloropalladium(II) adduct with dichloromethane (74 mg, 0.09 mmol) in anhydrous N,N-dimethylformamide (20 mL) was purged with nitrogen. Sodium bicarbonate (1.08 g, 13 mmol) as a suspension in 4 mL of water was added, and the mixture was purged with nitrogen again, and heated at 65° C. for 1 hour. After cooling, the reaction mixture was partitioned between ethyl acetate and brine. The organics were concentrated on a rotary evaporator. The residue was dissolved in ethanol, and heated with hydrazine (0.04 mL, 1.3 mmol) at 80° C. for 2 hours. After cooling, the precipitated solid was filtered and dried under vacuum to provide the title compound. MS (ESI) m/z 600 (M+H)$^+$.

Example 9C

6-[1-(phenylsulfonyl)-1H-pyrrolo[2,3-b]pyridin-3-yl]-4-(piperidin-4-ylmethyl)phthalazin-1(2H)-one A solution of EXAMPLE 9B (272 mg, 0.45 mmol) in dichloromethane (10 mL) was treated with trifluoroacetic acid (1 mL) at ambient temperature for 1 hour. Acetonitrile (10 mL) was added and the solution was concentrated on a rotary evaporator. The residue was purified by HPLC (Zorbax C-18, 0-100% gradient of acetonitrile in water containing 0.1% trifluoroacetic acid) to yield the title compound. MS (ESI) m/z 500 (M+H)$^+$; $^1$H NMR (300 MHz, CD$_3$OD) δ 1.49-1.66 (m, 2H), 2.01-2.16 (m, 2H), 2.26-2.37 (m, 1H), 2.93-3.05 (m, 2H), 3.10 (d, J=7.12 Hz, 2H), 3.39 (d, J=12.54 Hz, 2H), 7.41 (dd, J=8.14, 4.75 Hz, 1H), 7.55-7.61 (m, 2H), 7.64-7.72 (m, 1H), 8.18-8.24 (m, 3H), 8.24-8.27 (m, 1H), 8.33 (dd, J=7.97, 1.53 Hz, 1H), 8.39 (s, 1H), 8.45 (dd, J=4.92, 1.53 Hz, 1H), 8.47-8.52 (m, 1H).

Example 9D 4-(piperidin-4-ylmethyl)-6-(1H-pyrrolo[2,3-b]pyridin-3-yl)phthalazin-1(2H)-one To a flask containing EXAMPLE 9C (50 mg, 0.1 mmol) in ethanol was added potassium hydroxide (11 mg, 0.2 mmol), and the mixture was heated at 80° C. for 1 hour. After cooling, the mixture was concentrated on a rotary evaporator. The residue was purified by HPLC (Zorbax C-18, 0-100% gradient of acetonitrile in water containing 0.1% trifluoroacetic acid) to yield the title compound. MS (ESI) m/z 360 (M+H)$^+$; $^1$H NMR (300 MHz, DMSO-d$_6$) δ 1.36-1.53 (m, 2H), 1.83-1.98 (m, 2H), 2.07-2.22 (m, 1H), 2.81-2.95 (m, 2H), 2.95-3.04 (m, 2H), 3.26 (d, J=12.55 Hz, 2H), 7.24 (dd, J=7.80, 4.75 Hz, 1H), 8.15 (d, J=1.36 Hz, 1H), 8.22-8.24 (m, 1H), 8.25-8.27 (m, 1H), 8.29-8.33 (m, 1H), 8.34 (dd, J=4.75, 1.36 Hz, 1H), 8.42 (dd, J=7.80, 1.02 Hz, 1H), 8.43 (br s, 1H), 12.25 (br s, 1H), 12.45 (br s, 1H).

Example 10

4-(piperidin-2-ylmethyl)-6-(1H-pyrrolo[2,3-b]pyridin-3-yl)phthalazin-1(2H)-one

The title compound was prepared as described in EXAMPLE 9 substituting tert-butyl 2-formylpiperidine-1-carboxylate for tert-butyl 4-formylpiperidine-1-carboxylate. MS (ESI) m/z 360 (M+H)$^+$; $^1$H NMR (300 MHz, DMSO-d$_6$) δ 1.47-1.63 (m, 3H), 1.70-1.83 (m, 2H), 1.96-2.08 (m, 1H), 2.85-2.99 (m, 1H), 3.20-3.33 (m, 2H), 3.34-3.46 (m, 1H), 3.51-3.66 (m, 1H), 7.25 (dd, J=8.14, 4.75 Hz, 1H), 8.12-8.17 (m, 1H), 8.24 (d, J=2.71 Hz, 1H), 8.25-8.28 (m, 1H), 8.33 (d, J=8.48 Hz, 1H), 8.34-8.37 (m, 1H), 8.44 (dd, J=8.14, 1.02 Hz, 1H), 8.48 (br s, 1H), 12.28 (br s, 1H), 12.60 (br s, 1H).

Example 11

4-[4-(dimethylamino)benzyl]-6-(1H-pyrrolo[2,3-b]pyridin-3-yl)phthalazin-1(2H)-one The title compound was prepared as described in EXAMPLE 5, substituting 4-(dimethylamino)benzaldehyde for isonicotinaldehyde. MS (ESI) m/z 396 (M+H)$^+$; $^1$H NMR (300 MHz, DMSO-d$_6$) δ 2.90 (s, 6H), 4.30 (s, 2H), 6.83-6.94 (m, 2H), 7.15 (dd, J=7.80, 4.75 Hz, 1H), 7.23 (d, J=8.48 Hz, 2H), 7.87 (d, J=7.12 Hz, 1H), 8.04 (d, J=1.36 Hz, 1H), 8.10-8.16 (m, 2H), 8.23-8.28 (m, 1H), 8.32 (dd, J=4.75, 1.36 Hz, 1H), 12.19 (br s, 1H), 12.48 (br s, 1H).

Example 12

N-(4-{[4-oxo-7-(1H-pyrrolo[2,3-b]pyridin-3-yl)-3,4-dihydrophthalazin-1-yl]methyl}phenyl)acetamide The title compound was prepared as described in EXAMPLE 5, substituting N-(4-formylphenyl)acetamide for isonicotinaldehyde. MS (ESI) m/z 410 (M+H)$^+$; $^1$H NMR (300 MHz, DMSO-d$_6$) δ 2.00 (s, 3H), 4.34 (s, 2H), 7.14 (dd, J=8.14, 4.75 Hz, 1H), 7.23-7.31 (m, 2H), 7.52-7.60 (m, 2H), 7.74 (d, J=7.46 Hz, 1H), 7.99 (d, J=1.02 Hz, 1H), 8.10 (d, J=3.05 Hz, 1H), 8.11-8.16 (m, 1H), 8.23-8.27 (m, 1H), 8.30 (dd, J=4.75, 1.36 Hz, 1H), 9.90 (br s, 1H), 12.16 (br s, 1H), 12.51 (br s, 1H).

Example 13

4-[(1-methyl-1H-pyrazol-3-yl)methyl]-6-(1H-pyrrolo[2,3-b]pyridin-3-yl)phthalazin-1(2H)-one The title compound was prepared as described in EXAMPLE 5, substituting 1-methyl-1H-pyrazole-3-carbaldehyde for isonicotinaldehyde. MS (ESI) m/z 357 (M+H)$^+$; $^1$H NMR (300 MHz, DMSO-d$_6$) δ 3.79 (s, 3H), 4.27 (s, 2H), 6.08 (d, J=2.37 Hz, 1H), 7.27 (dd, J=8.14, 4.75 Hz, 1H), 7.59 (d, J=2.03 Hz, 1H), 8.18 (dd, J=7.29, 2.20 Hz, 2H), 8.22-8.25 (m, 1H), 8.27 (d, J=1.02 Hz, 1H), 8.34 (dd, J=4.75, 1.36 Hz, 1H), 8.40 (dd, J=7.97, 1.19 Hz, 1H), 12.20 (br s, 1H), 12.44 (br s, 1H).

Example 14

Enzyme Inhibition Data

This example describes the assays that may be used to identify compounds having kinase activity.

Cdc7 (BEV coexpressed huCDC7/DBF4) is prepared internally. Cdc7 assays are conducted as follows with final concentrations as listed. In 384-well v-bottom polypropylene plates, 6 μL compound (2% DMSO), is mixed with 6 μL of Cdc7 (2 ug/mL), and Jerini peptide substrate A-A11 (biotin-C$_6$linker-TPSDSLIYDDGLS) (2 μM), followed by immediate initiation with 6 μL λ-[$^{33}$P]-ATP (1 μM, 20 mCi/μmol) using a reaction buffer comprising 25 mM HEPES, pH 7.5, 1 mM DTT, 10 mM MgCl$_2$, 100 μM Na$_3$VO$_4$, 0.075 mg/ml Triton X-100. Reactions are quenched after 1 hr by the addition of 90 μL stop buffer (50 mM EDTA, 2M NaCl). 85 μL of the stopped reactions are transferred to 384-well streptavidin-coated plates (FlashPlate Plus, Perkin Elmer), incubated 30 minutes at room temperature and washed 3 times with 0.05% Tween-20/PBS using an ELX-405 automated plate washer (BioTek), and counted on a TopCount Scintillation Plate Reader (Packard). IC50 values are determined via non-linear regression fitting of enzyme inhibition data and corresponding Ki values are generated assuming ATP-competitive (equilibrium) inhibition and using the experimentally determined apparent ATP Km of 0.7 µM (as determined using the above assay condition, but varying ATP).

Table 1 depicts enzyme inhibition data ($K_i$) for exemplary compounds. In Table 1, "A" represents a $K_i$ of less than 10 nM, "B" represents a $K_i$ of between 10 nM and 100 nM, and "C" represents a $K_i$ of greater than 100 nM.

TABLE 1

| Example | Cdc7 Inhibition |
|---|---|
| 1 | A |
| 2 | C |
| 3 | B |
| 4 | C |
| 5 | A |
| 6 | C |
| 7 | C |
| 8 | A |
| 9 | B |
| 10 | C |
| 11 | B |
| 12 | A |
| 13 | B |

Compounds of the present invention assessed by the above-described assays were found to have Cdc7 kinase-inhibiting activity.

All publication and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

We claim:

1. A compound having formula (I)

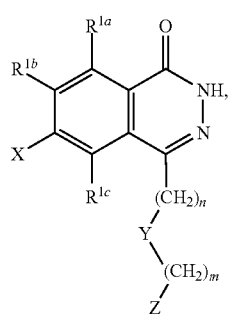

Formula (I)

wherein $R^{1a}$, $R^{1b}$, and $R^{1c}$ are independently hydrogen, hydroxy, nitro, halogen, cyano, trifluoromethyl, trifluoromethoxy, $C_{1-4}$-alkyl, —$OR^a$, or —$NR^bR^c$;

X is

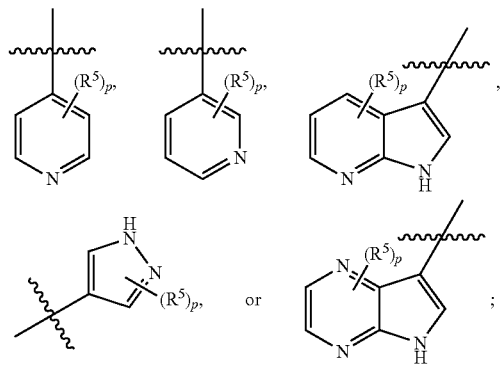

n is 0, 1, 2, or 3; provided that when n is 1, 2, or 3, m is 0;
m is 0, 1, 2, or 3; provided that when m is 1, 2, or 3, n is 0;
p is 0, 1, or 2;
Y is a bond, —O—, —C(O)—, —(O)C—, —C(O)O—, —OC(O)—, —$NR^e$—, —$NR^eC(O)$—, —$C(O)NR^e$—, —$NR^eC(O)NR^f$—, —$SO_2NR^e$—, or —$NR^eSO_2$—;
Z is

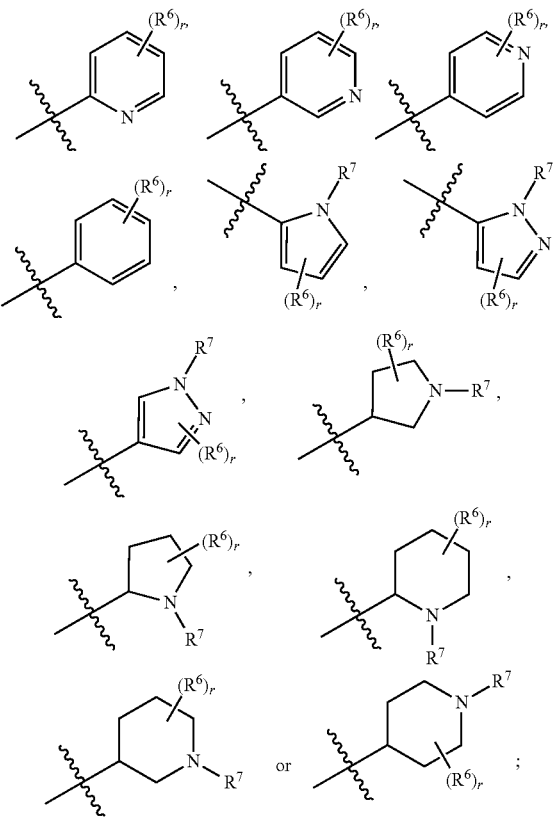

r is 0, 1, 2, or 3;
$R^5$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —NHC(O) $NHR^e$, —$NHSO_2R^d$, —$C(O)NR^eR^f$, —$SR^d$, —$S(O)R^d$, —$SO_2R^d$, —$SO_2NR^eNR^f$, —$B(OH)_2$, —$CF_3$, —$CF_2CF_3$, —$OCF_3$, and —$OCF_2CF_3$ wherein (a) the $R^5$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^g$, —$C(O)R^g$, —$C(O)OR^g$, —$OC(O)R^g$, —$NR^hR^i$, —$NR^hC(O)R^g$, —$NHSO_2R^g$, —$NHC(O)NHR^h$, —$C(O)NR^hR^i$; and wherein (b) the $R^5$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^j$, —$C(O)R^j$, —$C(O)OR^j$, —$OC(O)R^j$, —$NR^kR^l$, —$NR^kC(O)R^j$, —$NHC(O)NHR^k$, —$NHSO_2R^j$, —$C(O)NR^kR^l$, —$SR^j$, —$S(O)R^j$, —$SO_2R^j$, —$SO_2NR^kR^l$, —$CF_3$, —$CF_2CF_3$, —$OCF_3$, and —$OCF_2CF_3$;

$R^6$ is selected from the group consisting of $C_{1-8}$-alkyl, $C_{2-8}$-alkenyl, $C_{2-8}$-alkynyl, aryl, heterocyclyl, halogen, oxo, cyano, nitro, —$OR^d$, —$C(O)R^d$, —$C(O)OR^d$, —$OC(O)R^d$, —$NR^eR^f$, —$NR^eC(O)R^d$, —$NHC(O)NHR^e$, —$NHSO_2R^d$, —$C(O)NR^eR^f$, —$SR^d$, —$S(O)R^d$, —$SO_2R^d$, —$SO_2NR^eR^f$, —$B(OH)_2$, —$CF_3$, —$CF_2CF_3$, —$OCF_3$, and —$OCF_2CF_3$ wherein (a) the $R^6$ $C_{1-8}$-alkyl, $C_{2-8}$-alkenyl, and $C_{2-8}$-alkynyl, substituents are optionally substituted with one or more substituents selected from the group consisting of aryl, heterocyclyl, $C_{3-8}$-cycloalkyl, halogen, cyano, nitro, oxo, —$OR^g$, —$C(O)R^g$, —$C(O)OR^g$, —$OC(O)R^g$, —$NR^hR^i$, —$NR^hC(O)R^g$, —$NHSO_2R^g$, —$NHC(O)NHR^h$, —$C(O)NR^hR^i$; and wherein (b) the $R^6$ aryl and heterocyclyl substituents are optionally substituted with one or more substituents independently selected from the group consisting of $C_{1-8}$-alkyl, $C_{2-8}$-alkenyl, $C_{2-8}$-alkynyl, aryl, heterocyclyl, halogen, cyano, nitro, oxo —$OR^j$, —$C(O)R^j$, —$C(O)OR^j$, —$OC(O)R^j$, —$NR^kR^l$, —$NR^kC(O)R^j$, —$NHC(O)NHR^k$, —$NHSO_2R^j$, —$C(O)NR^kR^l$, —$SR^j$, —$S(O)R^j$, —$SO_2R^j$, —$SO_2NR^kR^l$, —$CF_3$, -$CF_2CF_3$, —$OCF_3$, and —$OCF_2CF_3$;

$R^7$ is hydrogen, $C_{1-8}$-alkyl or, —$C(O)C_{1-8}$-alkyl;

$R^a$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), —$O(C_{1-8}$-alkyl)$NH_2$, and —$N(C_{1-8}$-alkyl)$_2$;

$R^b$ and $R^c$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^b$ and $R^c$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^d$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, aryl-($C_{1-8}$-alkyl)-, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$; wherein the aryl, aryl-($C_{1-8}$-alkyl)-, heterocyclyl, and $C_{3-8}$-cycloalkyl, alone or as part of another group, are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, -$NH_2$, -$NH(C_{1-8}$-alkyl), and —$N(C_{1-8}$-alkyl)$_2$;

$R^e$ and $R^f$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^e$ and $R^f$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^g$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^h$ and $R^i$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^h$ and $R^i$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^j$, at each occurrence, is selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, wherein the $C_{1-8}$-alkyl, $C_{2-8}$-alkenyl, $C_{2-8}$-alkynyl, aryl, heterocyclyl, and $C_{3-8}$-cycloalkyl are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

$R^k$ and $R^l$, at each occurrence, are independently selected from the group consisting of hydrogen, $C_{1-8}$-alkyl, $C_{2-8}$-alkenyl, $C_{2-8}$-alkynyl, aryl, heterocyclyl, and $C_{3-8}$-cycloalkyl, and optionally, $R^k$ and $R^l$ can be joined together to form a 4-7 membered heterocycloalkyl ring, wherein the $C_{1-8}$-alkyl, $C_{2-8}$-alkenyl, $C_{2-8}$-alkynyl, aryl, heterocyclyl, $C_{3-8}$-cycloalkyl, and 4-7 membered heterocycloalkyl ring are optionally substituted with one or more substituents independently selected from the group consisting of $C_{1-8}$-alkyl, aryl, heterocyclyl, $C_{3-8}$-cycloalkyl, halogen, cyano, oxo, hydroxy, $C_{1-8}$-alkoxy, —$NH_2$, —$NH(C_{1-8}$-alkyl), and —$N(C_{1-8}$-alkyl)$_2$;

or a pharmaceutically acceptable salt thereof.

2. The compound of claim 1, wherein $R^{1a}$, $R^{1b}$, and $R^{1c}$ are hydrogen.

3. The compound of claim 1, wherein Y is a bond, n is 1, and m is 0.

4. The compound of claim 1, where wherein p is 0.

5. The compound of claim 1, wherein X is

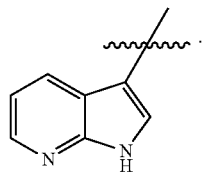 [SMILES: *c1c[nH]c2ncccc12]

6. The compound of claim 1, wherein $R^{1a}$, $R^{1b}$, and $R^{1c}$ are hydrogen, Y is a bond, and n is 1 and m is 0.

7. The compound of claim 1 which is
4-benzyl-6-(1H-pyrrolo[2,3-b]pyridin-3-yl)phthalazin-1(2H)-one;
4-benzyl-6-(pyridin-4-yl)phthalazin-1(2H)-one;
4-benzyl-6-(1H-pyrazol-4-yl)phthalazin-1(2H)-one;
4-benzyl-6-(pyridin-3-yl)phthalazin-1(2H)-one;
4-(pyridin-4-ylmethyl)-6-(1H-pyrrolo[2,3-b]pyridin-3-yl)phthalazin-1(2H)-one;
4-(2,5-dichlorobenzyl)-6-(1H-pyrrolo[2,3-b]pyridin-3-yl)phthalazin-1(2H)-one;
4-(piperidin-3-ylmethyl)-6-(1H-pyrrolo[2,3-b]pyridin-3-yl)phthalazin-1(2H)-one;
4-(pyridin-3-ylmethyl)-6-(1H-pyrrolo[2,3-b]pyridin-3-yl)phthalazin-1(2H)-one;
4-(piperidin-4-ylmethyl)-6-(1H-pyrrolo[2,3-b]pyridin-3-yl)phthalazin-1(2H)-one;
4-(piperidin-2-ylmethyl)-6-(1H-pyrrolo[2,3-b]pyridin-3-yl)phthalazin-1(2H)-one;
4-[4-(dimethylamino)benzyl]-6-(1H-pyrrolo[2,3-b]pyridin-3-yl)phthalazin-1(2H)-one;
N-(4-{[4-oxo-7-(1H-pyrrolo[2,3-b]pyridin-3-yl)-3,4-dihydrophthalazin-1-yl]methyl}phenyl)acetamide; or
4-[(1-methyl-1H-pyrazol-3-yl)methyl]-6-(1H-pyrrolo[2,3-b]pyridin-3-yl)phthalazin-1(2H)-one.

8. A pharmaceutical composition comprising a compound or pharmaceutically acceptable salt of claim 1 and pharmaceutically acceptable excipient.

* * * * *